US006461845B1

(12) United States Patent
Hagedorn

(10) Patent No.: US 6,461,845 B1
(45) Date of Patent: Oct. 8, 2002

(54) RECOMBINANT HEPATITIS C VIRUS RNA REPLICASE

(75) Inventor: Curt H. Hagedorn, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/597,877

(22) Filed: Jun. 20, 2000

Related U.S. Application Data

(63) Continuation-in-part of application No. 09/337,028, filed on Jun. 25, 1999, now Pat. No. 6,248,589, and a division of application No. 08/722,806, filed on Sep. 27, 1996, now Pat. No. 5,981,247.
(60) Provisional application No. 60/004,383, filed on Sep. 27, 1995.

(51) Int. Cl.[7] .................................................. C12N 9/12
(52) U.S. Cl. ........................................ 435/194; 435/440
(58) Field of Search ................................ 435/1.94, 440

(56) References Cited

U.S. PATENT DOCUMENTS 5,350,671 A    9/1994 Houghton et al. ............. 435/5

FOREIGN PATENT DOCUMENTS

| WO | 96/37619 | * 11/1996 |
| WO | 99/51781 | * 10/1999 |
| WO | 99/67396 | * 12/1999 |

OTHER PUBLICATIONS

Lohmann, V., et al. (1997) J. Virol. 71(11), 8416–8428.*
Al, R.H. et al. "Characterization of Active Hepatitis C Virus RNA–Dependent RNA Polymerase Expressed in *E. coli*"; Abstract presented at Cold Spring Harbor Meeting on *Molecular Approaches to the Control of Infectious Diseases*, held Sep. 9–13, 1996.
Al, R.H. et al. "Expression and Characterization of the NS5B (RNA–Dependent RNA Polymerase) Gene of Hepatitis C Virus"; Abstract of presentation at Meeting of American Association for the Study of Liver Diseases, held Nov. 3–7, 1995.
Al, R.H. et al. "Purification and Characterization of Recombinant Enzymatically Active, Hepatitis C RNA–Dependent RNA Polymerase (HCV rDRP)"; Abstract of presentation at annual Meetings of American Gastroenterological Association and American Association for the Study of Liver Diseases, held May 19–22, 1996.
Bartenschlager, R. et al. "Kinetic and Structural Analyses of Hepatitis C. Virus Polyprotein Processing"; (1994) *Journal of Virology* 68(8):5045–5055.
Behrens, S–E. et al. "Identification and properties of the RNA–dependent RNA polymerase of hepatitis C virus"; (1996) *The EMBO Journal* 15:12–22.
Choo, Q.–L. et al. "Genetic Organization and Diversity of the Hepatitis C Virus"; (1991) *Proc. Natl. Acad. Sci. USA* 88:2451–2455.

Grakoui, A. et al. "Expression and Identification of Hepatitis C Virus Polyprotein Cleavage Products" (1993) *Journal of Virology* 67:1385–1395.
Hagedorn, C.H. et al. "Expression in *E. coli* and Characterization of the Hepatitis C Virus NS5B Gene Product"; Abstract of Poster presentation at IRBM Workshop on *Molecular Mechanisms of RNA Replication*, held May 24–28, 1996, Alghero, Sardinia, Italy.
Hirowatari, Y. et al. "Expression and processing of putative nonstructural proteins of hepatitis C virus in insect cells using baculovirus vector"; (1995) *Virus Research* 35:43–61.
Koonin, E.V. "The Phylogeny of RNA–dependent RNA polymerases of positive–strand RNA viruses"; (1991) *Journal of General Virology* 72:2197–2206.
Kuo, G. et al. "An Assay for Circulating Antibodies to a Major Etiologic Virus of Human Non–A, Non–B Hepatitis"; (1989) *Science* 244:362–364.
Lin, C. et al. "Hepatitis C Virus NS3 Serine Proteinase: trans–Cleavage Requirements and Processing Kinetics"; (1994) *Journal of Virology* 68(12):8147–8157.
Lin, C. et al. Processing in the Hepatitis C Virus E2–NS2 Region: Identification of p7 and Two Distinct E2–Specific Products with Different C Termini; (1994) *Journal of Virology* 68:5063–5073.
Ohlmeyer, Michael H.J. et al. "Complex Synthetic Chemical Libraries indexed with Molecular Tags"; (1993) *Proc. Natl. Acad. Sci. USA* 90:10922–10926.
Rothstein, M.A. et al. "Enzymatic Activity of Poliovirus RNA Polymerase Synthesized in *Escherichia coli* from Viral cDNA"; (1988) *Virology* 164:301–308.
Sankar, S. et al. "Expression, Purification, and Properties of Recombinant Encephalomyocarditis Virus RNA–Dependent RNA Polymerase"; (1991) *Journal of Virology* 65:2993–3000.
Tanaka, T. et al. "A Novel Sequence Found at the 3'Terminus of Hepatitis C Virus Genome"; (1995) *Biochem. Biophys. Res. Commun.* 215:744–749.
Wu, J. et al Identifying Substrate Motifs of Protein Kinases by a Random Library Approach; (1994) *Biochemistry* 33:14825–14833.

* cited by examiner

*Primary Examiner*—Charles L. Patterson, Jr.
(74) *Attorney, Agent, or Firm*—Greenlee, Winner and Sullivan, P.C.

(57) ABSTRACT

A recombinant RNA-dependent RNA polymerase of hepatitis C virus (r-HCV-RDRP) coding DNA was cloned and expressed yielding active enzyme in vitro. The r-HCV-RDRP can include up to 20 added amino acids and up to nine deleted or substituted amino acids at the $NH_2$-terminus of the encoded amino acid sequence. The invention provides method to solubilize r-HCV-RDRP from a host cell lysate and purified r-HCV-RDRP. Methods for screening for inhibitors of r-HCV-RDRP in vitro, for making stably transfected mammalian cells expressing r-HCV-RDRP and for in vivo testing of r-HCV-RDRP inhibitors in vivo are disclosed. The invention provides antibodies to r-HCV-RDRP and methods for detecting antibodies to HCV-RDRP in serum of human patients.

5 Claims, 9 Drawing Sheets

$M_r \times 10^{-3}$

123 –

89 –

67 –  ← RDRP

50 –

38 –

1   2

RECOMBINANT HEPATITIS C VIRUS RNA REPLICASE

CROSS REFERENCE TO RELATED APPLICATIONS

This application claims priority from U.S. Provisional Application Ser. No. 60/004,383, filed Sep. 27, 1995, is a Division of U.S. patent application Ser. No. 08/722,806 filed Sep. 27, 1996, now issued as U.S. Pat. No. 5,981,247, and the present application is a continuation-in-part of U.S. patent application Ser. No. 09/337,028, filed Jun. 25, 1999 now U.S. Pat No. 6,248,589.

ACKNOWLEDGMENT OF FEDERAL RESEARCH SUPPORT

The United States Government has rights in this invention arising from National Institutes of Health Grant No. AI41424-01 which partially funded research leading to this invention.

FIELD OF THE INVENTION

The present invention relates Hepatitis-C virus (HCV), specifically to expression and purification of an RNA-dependent RNA polymerase (RDRP) encoded by the HCV genome, to antibodies directed against HCV-RDRP and to methods of using the enzyme to diagnose chronic HCV infections and to screen for antiviral agents effective against HCV.

BACKGROUND OF THE INVENTION

HCV is the major causative agent for post-transfusion and for sporadic non A, non B hepatitis (Alter, H. J. (1990) *J. Gastro. Hepatol.* 1:78–94; Dienstag, J. L. (1983) *Gastro* 85:439–462). Despite improved screening, HCV still accounts for at least 25 % of the acute viral hepatitis in many countries (Alter, H. J. (1990) supra; Dienstag, J. L. (1983) supra; Alter, M. J. et al. (1990a) *J.A.M.A.* 264:2231–2235; Alter, M. J. et al (1992) *N. Engl J. Med.* 327:1899–1905; Alter, M. J. et al .(1990b) *N. Engl J. Med.* 321:1494–1500). Infection by HCV is insidious in a high proportion of chronically infected (and infectious) carriers who may not experience clinical symptoms for many years. The high rate of progression of acute infection to chronic infection (70–100%) and liver disease (>50%), its world-wide distribution and lack of a vaccine make HCV a significant cause of morbidity and mortality.

HCV is an enveloped virus whose genome is a 9.5 kb single-stranded RNA (sense(+)) encoding a single polyprotein that is processed by proteolysis to yield at least 9 proteins. HCV is related to pestiviruses and flaviviruses (Choo, Q-L. et al. (1989) *Science* 244:362–364; Choo, Q-L. et al. (1991) *Proc. Natl. Acad. Sci. USA* 88:2451–2455. Reinfection of previously HCV-infected chimpanzees suggests that protective immunity is transient or non-existent (Farci, P. et al (1992) *Science* 258:135–140). Furthermore, results of recent vaccine trials suggest that development of an effective vaccine is remote (Houghton, M. et al. (1994) 2nd Internat. Meeting on Hepatitis C (San Diego)). Attempted treatment of chronic HCV infection using existing antiviral agents produces low cure rates and serious side effects. (Dienstag, J. L. (1983) supra.)

The nucleotide sequence of the HCV genome has been cloned and a single open reading frame has been identified. Using a vaccinia virus expression system, several cleavage products have been tentatively identified. (Lin, C. et al. (1994) *J. Virol.* 68:5063–5073; Grakoui, A. et al. (1993) *J. Virol.* 67:1385–1395.) The various putative cleavage products were recognized by antibodies raised against various peptides synthesized from amino acid sequences deduced from various segments of the coding regions. Sizes of antibody-reactive peptides were estimated by SDS-PAGE (See FIG. 1). The non-structural protein designated 5B (NS5B) has been shown to have an amino-terminal sequence SMSY (Ser-Met-Ser-Tyr). The NS5B region encodes a 68 kd protein (p68) which contains an internal GDD (Gly-Asp-Asp) motif found in RNA-dependent RNA polymerases of other RNA viruses (Koonin, E. V. (1991) *J. Gen. Virol.* 72:2197–2206). However, no polymerase activity has been detected for HCV p68. In fact, the question has been raised that the 5B protein (p68) alone does not encode an active RNA-dependent RNA polymerase enzyme and that another subunit, possibly the NS5A gene product, is essential to catalytic activity. Prior attempts by the inventors and others to express the NS5B coding region as a fusion protein, using existing expression systems that facilitate purification of the fusion product and specific cleavage have failed to yield any active polymerase.

HCV, in common with other RNA viruses that employ direct RNA-RNA replication, has a high mutation rate. Independent isolates of HCV RNA have numerous sequence differences. Hagedorn, et al., (2000) *Curr. Top. Microbiol. Immunol.* 242:225–260, reviewed sequence variation in the NS5B sequence of 48 independent isolates. While it was possible to identify regions of conserved sequence, the interpretation of the data is difficult because only a few were known to encode an active RDRP. Even fewer were known to be a sequence of an infectious virus.

At the present time, infectivity of a given HCV strain can only be demonstrated in tests in chimpanzees, which severely limits the number of strains which can be tested. The number of RDRP sequences which have been tested for activity is limited, as described herein, by the necessity of modifying the N-terminus of the NS5B sequence to permit independent expression of RDRP in a recombinant host cell. Subsequent to the original priority hereof, others have isolated and expressed active RDRP. Lohmann, V., et al (1997) *J. Virol.* 71:8416–8428 GenBank Z97730, reported an active clone of HCV type 1b. The enzyme was shown to be active after deletion of either 25 or 55 amino acids of the C-terminus. Addition of an oligo-his tag permitted purification by nickel affinity chromatography of enzyme expressed in insect cells. Yamashita, T., et al (1998) *J. Biol. Chem.* 273:15479–15486 prepared an active RDRP from a clone of type 1b-JK1 (GenBank X65196). The authors thereof prepared a C-terminally deleted (Δ21) RDRP fusion protein with glutathione-S transferase (GST) attached at the N-terminus. The enzyme was expressed in *E. coli*, yielding active enzyme with or without the GST tag, which served as an affinity purification ligand. The authors also reported three single amino acid replacements which abolished activity. Ferrari, E., et al (1999) reported several C-terminal deletion constructs Δ16,19 21, 55 and 63 combined with oligo-his tags at either the N- or C-terminus. The enzymes were expressed in *E. coli* cells and purified with a chelated nickel column. RDRP enzymes of two HCV strains were studied, a 1a "H77" or "Hutchinson" isolate and a 1*b* "BK" isolate, although the RN sequences of the strains were not specifically identified. The oligo-his tags did not destroy activity, however enzymes having a C-terminal oligo-his tag had greater activity in an assay using a poly(C) homopolymer template. Luo, G.et al,(2000) *J. Virol.* 74:851–863 reported isolation of several NS5B clones from serum of an infected patient. Nearly half of the isolates had little or no RDRP activity. One isolate, which had the highest in vitro activity, was found to have a stop codon resulting in a deletion of 18 C-terminal amino acids. $Mn^{++}$ was found to stimulate activity 20-fold compared to the activity in the presence of $Mg^{++}$. No nucleotide or amino acid sequences were reported. Patent publication No. WO 99/29843 disclosed an isolated NS5B sequence and encoded RDRP, both full length and having a 21 amino acid deletion at the C-terminus. The source of the HCV was not given although the sequences appear to be related to type 1a. No data regarding activity of the encoded RDRP was disclosed. For a recent review, see Hagedorn, C. et al. (2000).

SUMMARY OF THE INVENTION

The present invention provides methods for making modified structures of the HCV-RDRP. The need to make modifications is due to the quasi-species nature of the virus, the fact that the protein appears intracellularly as the product of post-translational cleavage of a polyprotein, and in vitro insolubility of the isolated enzyme. The modifications described herein enable translation of the NS5B region of HCV RNA in transformed host cells, without the necessity of translating other virus-coded proteins at the same time. The second category relates to modifications at the C-terminus that contribute to solubility of the enzyme in aqueous media. The third category relates to individual amino acid substitutions which can be introduced to individual isolates encoding HCV-RDRP to enhance enzyme properties. As a consequence of the high mutation rate that occurs during HCV replication, individual isolates encode RDRP variants that vary in primary sequence and in functional attributes. These include, for example, reaction rate, template specificity, processivity, ease of purification, stability during purification and during storage and the like. Other advantages of the modifications will be apparent to those of ordinary skill in the art from the description herein.

The present invention provides a recombinant protein of HCV having RDRP activity (r-HCV-RDRP) obtainable by expression in a host eukaryote or prokaryote cell of a modified NS5B coding region of HCV. The modification includes addition at the amino terminus of a methionine residue and optionally from 1–20 additional amino acids interposed between the N-terminal methionine and the N-terminal serine of unmodified NS5B gene product. The modification also includes deletion at the amino terminus of up to 9 amino acids to provide an amino-terminal methionine. Two methionines occur naturally according to the deduced sequence of wild-type HCV-RDRP. Therefore, modification includes deletion to remove amino acids lying N-terminal to either methionine or, alternatively, deletion to some intermediate point between the two methionines plus addition of an N-terminal methionine codon. Other optional modifications include deletion of from 18 to 60 C-terminal amino acids and various amino acid substitutions throughout the protein, as described in detail herein. Deletion at the C-terminus improves solubility of isolated NS5B protein, without destroying activity, in in vitro assays. Individual amino acid substitutions in the protein can enhance enzyme specific activity, stability during purification, template specificity and other properties as described herein. A combination of deletions and insertions, within the limits described is also contemplated. Added amino acid sequence can be devised to create a specific protease cleavage site to permit post translational modification of the recombinant HCV-RDRP expression produce, in vivo or in vitro. Such post-transcriptional modification can be used to generate exactly the amino acid sequence encoded by NS5B, having an N-terminal serine. Added amino acid sequence can be devised to generate an affinity ligand binding site, for convenience and ease of purification. The data reported herein were obtained with a r-HCV-RDRP having an N-terminal MA (Met-Ala) dipeptide, giving an N-terminal sequence MASMSY (SEQ ID NO:6) instead of the predicted SMSY sequence of the most natural isolates of HCV NS5B protein. The coding sequence of NS5B is accordingly modified to include a met codon (ATG) at the 5'-end, as well as, optionally, codons for other amino acids to be included or deleted. Minimal modifications are preferred, in order to avoid potential deleterious effects on enzyme activity, and to avoid creating artificial epitopes. The r-HCV-RDRP can be expressed in procaryotic or eucaryotic cells to yield active RDRP. The expression of active r-HCV-RDRP in *E. coli* demonstrates that no other HCV-encoded protein is necessary for polymerase activity.

Individual isolates of HCV-RDRP differ widely in their activity, due to differences in amino acid sequence. The present invention introduces the concept of an optimized sequence, whereby specific, directed amino acid substitutions are made, starting from a single original isolate. Individual amino acid substitutions are generated by a series of site specific mutations of the coding region of the original isolate, using known methods. The purpose of the site-specific amino acid substitutions is to enhance catalytic properties of the enzyme. Such properties include, but are not limited to, reaction rate, template specificity, processivity, yield of full length products, ease of purification, and stability, both during purification and during storage, and adaptability to an in vivo assay.

The invention further provides methods for rapid and efficient purification of an r-HCV-RDRP expressed in procaryotic cells, allowing for milligram quantity preparations or r-HCV-RDRP at a purity of at least 95 % as determined by SDS-PAGE (See FIG. 9).

The invention further provides r-HCV-RDRP in solubilized form, and a method of solubilization without destroying activity.

The invention also provides methods for purifying solubilized HCV-RDRP. One such method, to be used in combination with others, is affinity chromatography, using antibody to r-HCV-RDRP as the affinity ligand. Other affinity ligands are obtained by a combinatorial library approach as described, e.g., by Wu, J. et al. (1994) *Biochemistry* 33:14825–14833; and Ohlmeyer, M. H. J. et al. (1993) *Procl. Nat. Acad. Sci. USA* 90:10922–10926.

The invention also provides for enzyme sequence modification by adding an affinity tag to enhance ease of purification. The use of an oligo-histidine tag for purification by chromatography on a chelated metal column is described herein.

In addition, the invention provides polyclonal or monoclonal antibodies specific for HCV-RDRP. Such antibodies can be made by known techniques, using the purified enzyme as antigen. Such antibodies bind either r-HCV-RDRP or wild-type HCV-RDRP. The availability of such antibodies makes it possible to prepare an affinity-labeled chromatography matrix for rapid purification of HCV-RDRP. The antibody also makes possible rapid detection of HCV-RDRP in biological materials, for example, in serum of HCV-infected patients.

The invention further provides a method for transfecting a mammalian cell with HCV-RDRP and expressing the enzyme within the cell. Consequently, the invention also provides a transfected mammalian cell line expressing r-HCV-RDRP. Such cells are useful for assaying the effects of candidate anti-viral compounds as inhibitors of RDRP activity. For measuring activity in mammalian cells, the full length enzyme having an intact C-terminal sequence (untruncated) is considered to be the form most likely to respond to potential inhibitors as the viral enzyme would in infected cells.

Therefore, the invention also provides a method for screening possible inhibitors of RDRP activity in vivo. Compounds with inhibitory activity can have anti-viral activity, since inhibition of the polymerase inhibits viral replication and expression of virus gene products. The in vitro assay is advantageous because it can rule out compounds which cannot enter the infected cell. One class of attractive candidate compounds is the nucleoside analogs; compounds which after being modified (phosphorylated) within cells can bind to substrate sites on the enzyme or which can be incorporated into a newly synthesized RNA but whose presence there disrupts normal function of the HCV polymerase or further replication of an RNA containing the analog. Acyclovir is one example of a very effective and safe nucleoside analogue that inhibits DNA virus replication by inhibiting a viral polymerase (DNA-dependent DNA polymerase) and interfering with primer-template function (chain termination). Such analogs are almost always effective only in the nucleotide triphosphate form. The in vitro assay provides a convenient method of administering the compound in its nucleoside form or nucleoside monophosphate form, allowing endogenous metabolic activity of the cell to convert that form to the active triphosphate, thereby avoiding a step of chemical synthesis of the triphosphate, as would be required for an in vivo assay.

A method for measuring HCV-RDRP activity in vitro is also provided. Such an assay permits identification of the enzyme and evaluation of its concentration during purification. In addition, the assay provides an additional, in vitro, method for screening potential inhibitors of RDRP as candidate anti-viral agents.

In principle, any compound can be tested as a candidate RDRP inhibitor. Certain classes of compounds are considered attractive candidates. These include, without limitation, nucleoside analogs, oligonucleotides and peptides. Certain compounds having planar, polycyclic-aromatic characteristics are also potential inhibitors. It will be understood that compounds identified as effective RDRP inhibitors must be further screened for toxicity, bioavailability, side effects and the like before being tested as therapeutic agents. Nevertheless, the initial identification as an inhibitor of HCV-RDRP is an essential first step in the development of an anti-viral therapy. It will also be recognized that an inhibitor of r-HCV-RDRP will also inhibit wild-type HCV-RDRP.

In another aspect of the invention, the existence of purified HCV-RDRP or r-HCV-RDRP makes it possible to detect and measure antibodies to RDRP present in the serum of an HCV-infected patient. The fact that such antibodies exist at all is in itself a finding made possible by the expression and preparation of purified r-HCV-RDRP according to the invention. The existence of circulating antibodies to HCV-RDRP in infected serum may be due to lysis of infected cells and release of HCV-RDRP into the extracellular fluids and bloodstream, where it can stimulate an antibody response. As the disease fluctuates in severity, the amounts of HCV-RDRP released and the amounts of antibody thereto would also fluctuate. Therefore, the amount of antibody to HCV-RDRP present in a patient's serum can be used as an indicator, not only of the presence of infection, but of its severity at a given time. The assay for anti-HCV-RDRP can serve as a means of diagnosing infection and also as a means of monitoring the course of the disease over time or in response to treatment. The assay for anti-HCV-RDRP can be carried out by a variety of known techniques, such as the gel separation method described herein. Other suitable methods include ELISA, and radioimmunoassay. A sandwich-type assay, using immobilized r-HCV-RDRP to capture the antibody can then use an anti-immunoglobulin reagent tagged with an appropriate marker such as an enzyme, radioisotope, fluorescent molecule or chemiluminescent marker or the like, all as understood by those skilled in the art. (*Antibodies: A laboratory manual*, Ed Harlow and David Lane, Cold Spring Harbor Laboratory (1988) pp. 553–611.)

DETAILED DESCRIPTION OF THE INVENTION

Definitions

Figure 1:
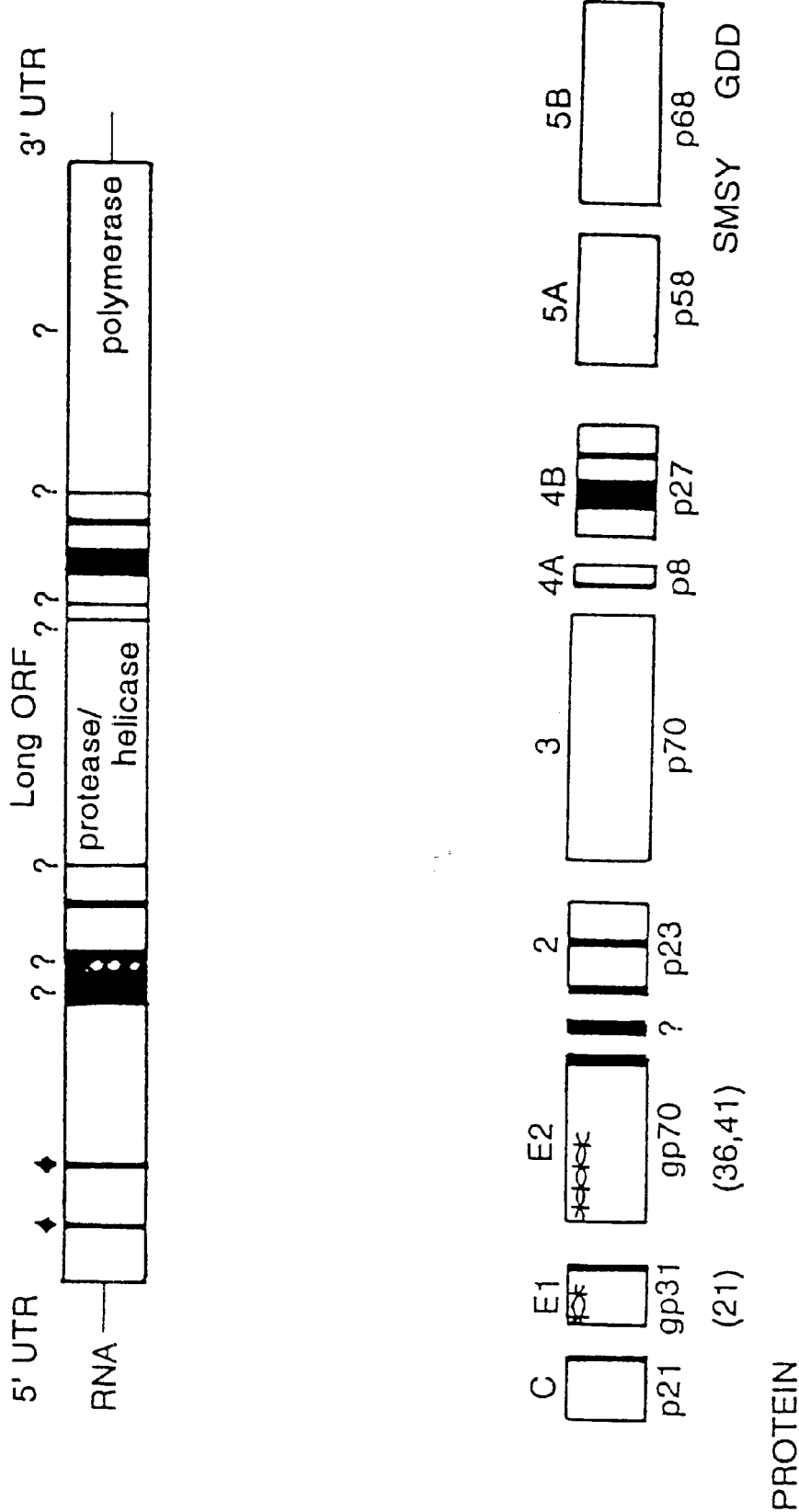
FIG. 1. Hepatitis C virus genome and polyprotein cleavage products. The cleavage products of the HCV polyprotein have been tentatively identified using vaccina virus expression systems. The amino terminus of the 5B protein expressed and processed in this system is SMSY (Ser-Met-Ser-Tyr). Although published reports have not proved that the 5B protein has RNA polymerase activity, it does contain the GDD (Gly-Asp-Asp) motif found in other RNA-dependent RNA polymerases. The question has been raised that the 5B protein alone does not encode an active RNA-dependent RNA polymerase enzyme and that another subunit (possibly the NS5A gene product) is essential for catalytic activity. During the initial phases of this work we were unsure if the protein encoded by NS5B would exhibit RNA-dependent RNA polymerase activity simply due to the lack of other essential factors.
Figure 2:
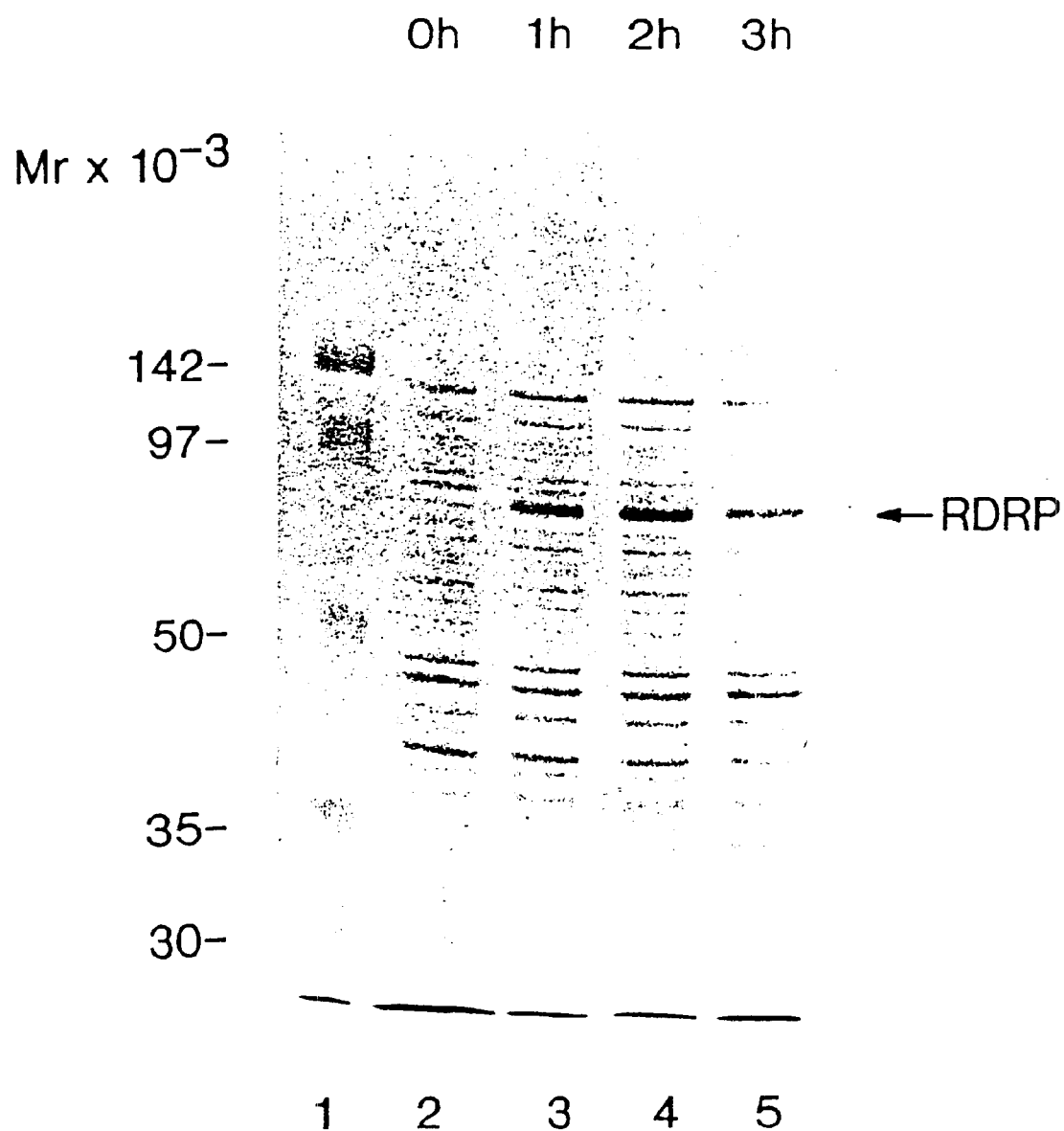
FIG. 2. Expression of r-HCV RNA-dependent RNA polymerase in *E. coli* using the T7 polymerase driven Studier vectors. *E. coli* containing the engineering T7 polymerase driven expression vector were incubated at 37° C. until an $OD_{600}$ of 0.6 was reached. A sample of cells was obtained and IPTG added to a final concentration of 1 mM. Samples were collected at 1, 2 and 3 hours after IPTG induction. Whole cells were lysed in 1× sample buffer at 95° C. and samples analyzed by 10% SDS-PAGE. The photograph shows a representative Coomassie Blue stained gel. Lane 1 represents molecular mass markers; lane 2, the uninduced control (0 h); lane 3, 1 h; lane 4, 2 h; and lane 5, 3 h after IPTG induction. Recombinant r-HCV RNA-dependent RNA polymerase is indicated by an arrow (RDRP).
Figure 3:
FIG. 3. Some patients with chronic hepatitis C have circulating antibodies that react with recombinant HCV RNA-dependent RNA polymerase. Cells expressing r-HCV RDRP were harvested and lysed by heating in SDS-PAGE sample buffer. Soluble proteins were separated by SDS-PAGE, transferred to nitrocellulose membranes and immunoblotted with human sera using an Immunetics Miniblotter template (Hagedorn, et al. *FEBS Lett*. (1990) 264:59–62). Immunoblots were developed with a secondary anti-human horseradish peroxidase conjugated antibody and enhanced chemiluminescent methods (ECL, Amersham). This photograph shows an immunoblot where lane 1 was probed with normal human serum and lanes 2 (1:500 dilution), 3 (1:300), and 4 (1:200) were probed with serum from a patient with chronic hepatitis C. The location of recombinant HCV RDRP (visualized by Coomassie and Ponceau S staining) is indicated by an arrow. These lower molecular mass bands seen in lanes 3 & 4 represent proteolytic fragments of RDRP seen when whole *E. coli* lysates are used in immunoblots.
Figure 4:
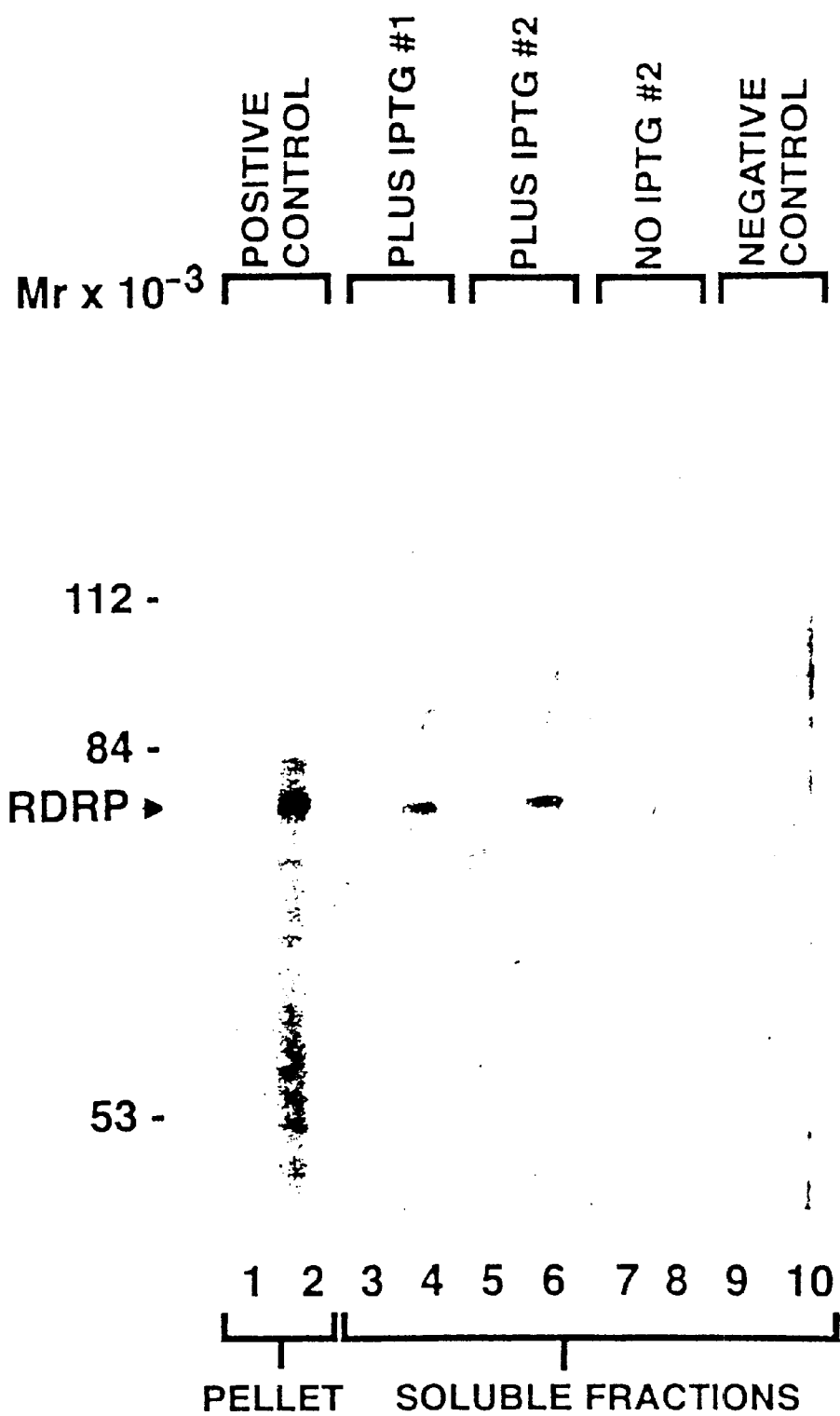
FIG. 4. Solubilization of HCV RDRP under nondenaturing conditions. Cells expressing r-HCV RDRP were harvested and processed using standard methods. Samples of insoluble E. coli pellets (pellet, positive control) and soluble fractions from cells containing or not containing (negative control) the RDRP expression vector were separated by SDS-PAGE and transferred to nitrocellulose membranes. Proteins bound to nitrocellulose were probed with rabbit preimmune and rabbit anti-RDRP sera as outlined in FIG. 3. Blots were developed with the ECL system (Amersham). The photograph shows an immunoblot where lanes 1,3,5,7 and 9 were probed with preimmune serum and lanes 2,4,6,8 and 10 were probed with immune serum. Two independently prepared samples of soluble proteins (plus IPTC #1 & #2, lanes 3–6) were examined.
Figure 5:
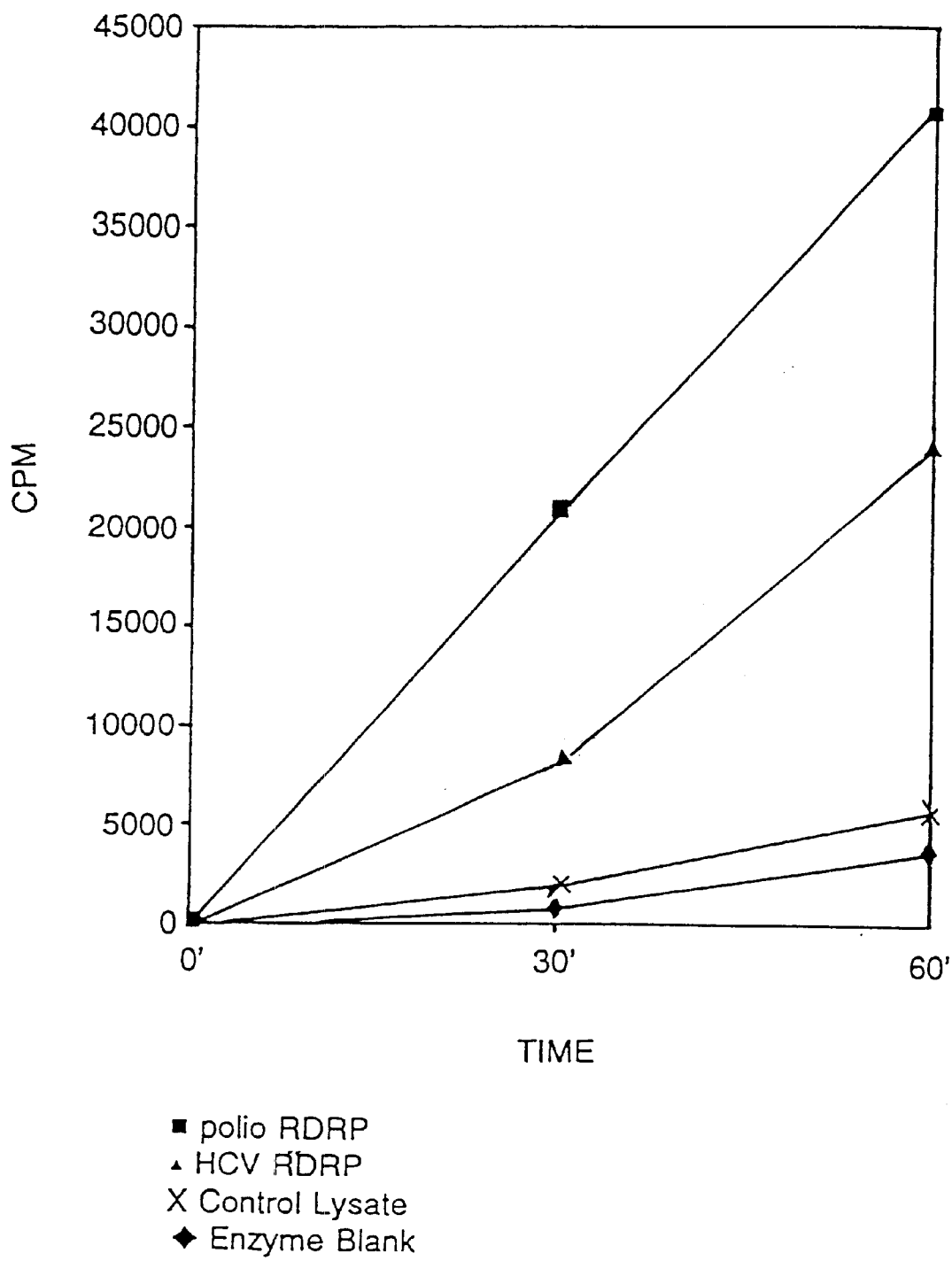
FIG. 5. Enzymatically active recombinant r-HCV RNA-dependent RNA polymerase. Poly(U) polymerase activity of purified recombinant poliovirus RDRP (approximately 50 ng) and equal quantities of soluble protein (approximately 1 $\mu$g) from E. coli expressing r-HCV RDRP (HCV RDRP lysate) or control cells not expressing RDRP (control lysate) are shown. Incubations were performed as described previously and CPM of poly(U) recovered from 15 $\mu$l of incubation are shown at 30 min (one sample) and 60 min (mean of duplicates) of incubation are shown (J. Virol. (1986) 58:790–796).
Figure 6:
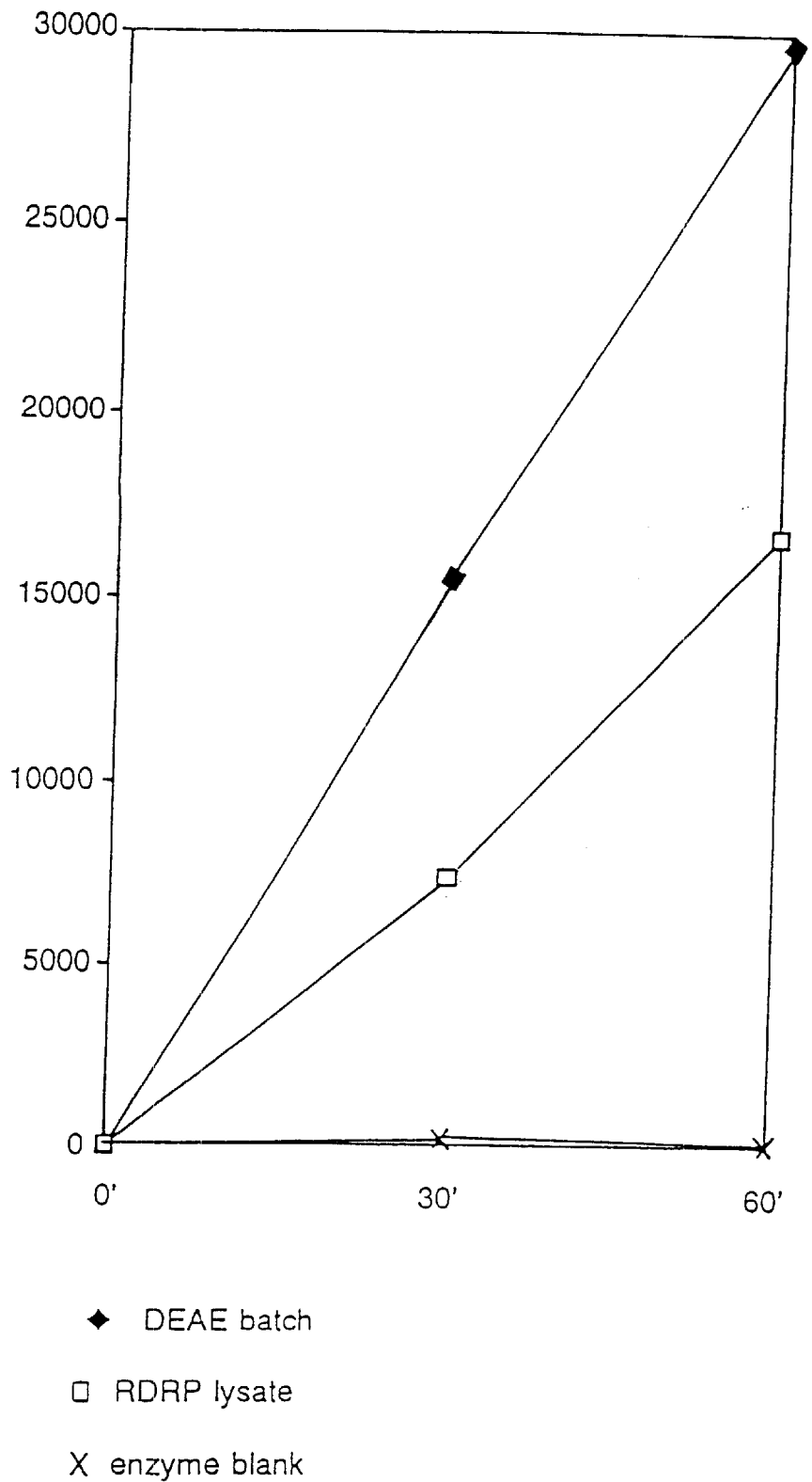
FIG. 6. Enzyme assay of partially purified recombinant HCV RNA-dependent RNA polymerase. Lysates of E. coli expressing r-HCV RDRP were prepared and enzyme assays performed as in FIG. 5. The experiment shown used a DEAE resin in a batch purification approach under pH and buffer conditions that allow RDRP to bind the resin. Equal quantities of protein were assayed from cell lysates (designated RDRP lysate) and proteins eluted from DEAE resin with 0.5 M NaCl (designated DEAE batch) that were concentrated to approximately that of the lysate. Additional studies with DEAE resin and other test resins have shown that partial purification of RDRP enzyme activity correlates with increases in the amount of unproteolyzed RDRP that we detect by immunoblotting using rabbit antiserum and the methods outlined in FIG. 4.
Figure 7:
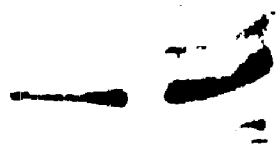
FIG. 7. Immunoaffinity purification of recombinant r-HCV RDRP. SDS-PAGE separation and immunoblotting data following purification by an immunoaffinity column prepared with rabbit polyclonal protein A Sepharose purified anti-RDRP antibodies. The starting material was protein solubilized from E. coli expressing recombinant r-HCV RDRP. The figure shows an immunoblot of proteins that were eluted from two identical columns that had protein applied under different detergent conditions. Lane 1 depicts proteins eluted from antibody/Sepharose beads that had been mixed overnight with the solubilized recombinant RDRP in 20 mM Tris-pH 7.5, 100 mM KCl, 0.5 mM EdTA, 1 mM DTT, 5% glycerol, and 0.05% Triton X-100. These beads were washed the following morning with 10 mM potassium phosphate buffer-pH 7.2 and proteins eluted with 100 mM glycine-pH 2.5. The eluted protein was collected in 1 M Tris-pH 8.0 to readjust the pH. Proteins eluted from the column were then analyzed by SDS-PAGE and immunoblotting as in FIG. 4. Lane 2 depicts proteins eluted from identical beads mixed with the same starting material except that 0.05 % NP-40 was present instead of 0.05 % Triton X-100. The location of r-HCV RDRP is indicated.

"RDRP" stands for RNA-dependent RNA polymerase, an enzyme catalyzing RNA synthesis, using a single-stranded RNA template, the synthesized RNA having a sequence complementary to an RNA template. "HCV-RDRP" is an RDRP of Hepatitis C virus. A modified HCV-RDRP described herein is designated r-HCV-RDRP. The region of the HCV genome designated NS5B has been identified as a protein cleavage product of the HCV polyprotein, using a vaccinia virus expression system as described supra. The nucleotide sequence of NS5B (strain 1a) is included in SEQ ID NO: 1. Putative amino acid coding by the NS5B sequence of SEQ ID NO: 1 begins with nucleotide 7. Where the sequence has been deleted at the 5' end, the remaining sequence has been designated by the nucleotide numbers beginning and ending the remaining coding sequences, not including the stop codon. For example $NS5B_{34-1779}$ designates that part of NS5B including nucleotides 34–1779 of the NS5B coding region.

The amino acid sequence of a r-HCV-RDRP of strain 1a of HCV is given in SEQ ID NO:2. The amino acid sequence of the strain 1aNS5B begins at amino acid No. 3 of SEQ ID NO:2. Where the sequence encoded by a NS5B has been deleted al the N-terminus, the remaining sequence is designated $\Delta^n NS5B$ where n is the number of amino acids deleted from the N-terminus of the NS5B. For example a type 1a $\Delta^9$ NS5B designates the sequence of amino acids 12–593 in SEQ ID NO:2.

Various r-HCV-RDRP constructs are contemplated according to the invention, as described. Coding sequences modified at the N-terminus included with the invention have the general sequence ATG-$N_x$-($N^S$)($N^M$)($N^S$)($N^Y$)($N^S$)($N^W$)($N^T$)($N^G$)($N^A$)-[$NS5B_{34-1779}$] where $N_x$ is any nucleotide sequence encoding from 0–20 amino acids, $N^S$ is a codon encoding serine, $N^M$ is a codon encoding methionine, $N^Y$ is a codon encoding tyrosine, $N^W$ is a codon encoding tryptophane, $N^T$ is a codon encoding threonine, $N^G$ is a codon encoding glutamic acid, and $N^A$ is a codon encoding alanine, and $NS5B_{34-1779}$ is the remaining coding sequence. Any of the codons in parentheses can be deleted, if desired. Up to 5 of the codons in parentheses can be mutated if desired. The term "mutated" is intended to mean altered to encode an amino acid other than that originally encoded by the NS5B sequence. For example, individual codons can be altered to encode alanine, by the known method of alanine scanning mutagenesis. Alanine scanning mutagenesis provides a rapid and convenient method for identifying amino acid positions where substitution is tolerated, without substantially affecting function negatively. Positions where alanine scanning reveals tolerance for substitution are likely to tolerate other amino acid substituents as well. Preferred substituents are one or more histidine residues, which can serve as affinity ligands for metal (e.g. nickel) columns. The presence of histidine provides preferential binding to the column to facilitate purification of r-HCV-RDRP. [$NS5B_{34-1779}$], as defined, represents the nucleotide sequence encoding the remainder of an NS5B protein from nucleotides 34–1779, not including the stop codon. It will be understood that many NS5B sequences are known, generated by the high error rate of RNA dependent RNA polymerases or by the lack of an error correction function in the process of RNA dependent RNA replication. See Holland, et al. (1992) and Buck (1996). The detailed nucleotide sequence of NS5B of any isolate of HCV is likely to differ from that of another isolate. The differences of nucleotide sequence are often reflected in variations of amino acid sequence. The notation $NS5B_{34-1449}$ is used herein to designate any sequence encoding 582 amino acids of C-terminal sequence of an active enzyme, unless a specific strain is also designated. The techniques for making any of the foregoing sequences are essentially as described below for the sequence where $N_x$ is GCT and none of the codons in parentheses, encoding the first nine amino acids encoded by NS5B, is deleted. It will be apparent that primers can be synthesized for the desired sequence combined with desired restriction site sequences to facilitate insertion into appropriate expression vectors. The choice of vector is based on factors known in the art, including the host cell, the type of promoter desired and the presence or absence of additional sequences which could be co-expressed with the r-HCV-RDRP. The reaction condition, PCR, vector insertion and host cell growth are as described below or as well-known in the art.

Other modifications can be made to r-HCV-RDRP. A deletion of approximately 25 % of the C-terminal region that did not include the Gly-Asp-Asp motif was constructed (r-HCV-RDRP-ΔC) and tested for activity. Although protein was expressed and was detectable by immunoblotting with anti-RDRP serum, lysate of *E. coli* expressing r-HCV-RDRP-ΔC had no measurable activity in either the poly(U) assay or with globin mRNA as template. However, the region of amino acids 565–572 of HCV-RDRP (565–572 of SEQ ID NO:2) near the C-terminus is considered to be exposed at the protein surface on the basis of modeling studies. Site directed mutagenesis has been used to alter the coding to Arg 570→His, Arg 572→His and Trp 573→His (using the numbering of SEQ ID NO:2). By clustering one or more additional histidine residues in a surface region near one end of the protein, purification by metal-affinity chromatography is facilitated while enzymatic activity is not substantially affected. Other predicted surface regions that can serve as sites for mutagenesis to replace an existing amino acid with histidine include amino acids 47–56, 152–159, 183–184, 210–215, 269–272, 384–391, and 439–442 in SEQ ID NO:2.Deletions of various lengths of the C-terminal amino acids were made. As many as 60 amino acids of the C-terminal sequence can be deleted without significant loss of activity. The C-terminal 21 amino acids are mostly hydrophobic and contribute to the insolubility of the isolated RDRP enzyme. Further deletion (more than 21 amino acids) can contribute to increased activity by removing a non-structural region. Modifications that include a C-terminal deletion are designated by the symbols "CΔ" followed by a number denoting the number of deleted amino acids.

Although the r-HCV-RDRP can be expressed in virtually any host cell type, the enzyme should preferably be in soluble form in order to be useful in in vitro studies, such as testing for inhibitors. When synthesized intracellularly, the enzyme is in an insoluble form in cell lysates unless steps are taken to solubilize the enzyme. In general, host cells are collected and concentrated, then lysed by means known to disrupt the host cells, for example by the use of a host-cell-wall hydrolyzing enzyme, by sonication and the like. In general a protease inhibitor is added to protect against proteolytic enzymes released by cell lysis. A non-ionic detergent can also be employed. Sonicated cells and sub-cellular complexes are subjected to freezing and thawing in the presence of the above-named components. Remaining particulate matter is removed by centrifugation at 10,000–35,000×g. The r-HCV-RDRP remains in the supernatant. A detailed protocol for solubilizing r-HCV-RDRP expressed in *E. coli* is described below.

Deleting the hydrophobic tail of the enzyme results in increased aqueous solubility of the enzyme. The C-terminal deletion of 21–60 amino acids is a preferred modification for making an RDRP to be used in vitro.

An optimized RDRP amino acid sequence can be developed by analyzing isolated sequences and choosing conserved amino acids wherever such a choice appears likely to result in an active enzyme. Two such optimized sequences have been made, shown in Tables 1 and 2, respectively, set forth in single letter amino acid code. Further optimization of the "template" sequences of Tables 1 and 2 can be achieved through specific amino acid substitutions described herein. The template sequence of Table 1 (SEQ ID NO: 12) can be further modified to enhance enzyme properties by making one or more of the following amino acid substitutions: preferred substitutions are Q21 to S or E; Q67 to R or K; R100 to K; R116 to K; A133 to E or V; A220 to S; V340 to A; or T302 to S. Also preferred, with lower priority, are the following amino acid substitutions, one or more of which can be introduced as desired: K533 to R; A209 to T; Q49 to L; S233 to N; K512 to R; or G551 to S. For enzyme intended for expression and assay in vivo, the following amino acid substitutions can be made in the membrane anchoring domain: M575 to W; W576 to F; S582 to A; or V583 to K. The foregoing amino acid position numbers are those used in Table 1. DNA encoding the template amino acid sequences of Table 1 or Table 2 can be acquired by modifying any of the cloned sequences known in the art, using codons based on the genetic code and codon selection criteria based on codons preferred for the intended expression host. For preparation of large quantities of enzyme, or for in vitro assays, codons preferred for *E. coli* are recommended, while enzyme intended for expression and assay in vivo, in eukaryotic cells, can be encoded with codons preferred in eukaryotes. Known methods for sequence modification, using oligonucleotide synthesis, polymerase chain reaction and the like can be used to prepare the desired coding DNA. Specific oligonucleotide primers for making the foregoing preferred modifications are described in Example 2. Properties which can be enhanced by such replacements include enzyme activity, template specificity, processivity, stability in vitro or in vivo, stability during purification, adaptability to an in vivo assay, crystallizability, and the like.

The template sequence of Table 2 (SEQ ID NO:23) can be further modified to enhance enzyme properties by making one or more of the following amino acid substitutions, the preferred substitutions being: Q21 to S or E; Q67 to R, R116 to K; E133 to V; C215 to T or N; K256 to R; S302 to T or R; N318 to C; V340 to A; E466 to Q; K512 to R or A, or K533 to R. Methods for making the foregoing modifications are essentially as shown herein for the template sequence of Table 1, with appropriate modification, as dictated by the particular amino acid substitutions desired. An especially preferred modification of the template of Table 2 is prepared by making the following amino acid substitutions: Glu at position 21; Arg at position 67; K at position 116; Val at position 133; Asn at position 215; and Ala at position 512. The resulting RDRP is optimized for ease of crystallization.

Further purification of the enzyme is accomplished by techniques and expedients known in the art. These include, but are not limited to, antibody affinity chromatography, metal-binding affinity chromatography (a technique especially suited for modified forms of the enzyme having added histidine residues) as well as conventional ion-exchange columns, differential precipitation with ammonium sulfate and other methods known in the art, not limited to the methods specifically disclosed herein. "Purified form" is used herein to mean any preparation of the enzyme having at least 4-fold greater specific activity than that measured in a solubilized cell lysate. An oligo-histidine tail can be added to the new carboxy terminus of C-terminal deleted RDRP for ease of purification, without significantly affecting activity. Preferred oligo-his tails of the invention include (using single4letter code) LEH$_6$, A$_n$SH$_6$, and G$_n$SH$_6$. The oligo-his tail provides an affinity ligand for metal-binding affinity chromatography using a chelated-nickel column, according to the literature. However, a feature of the present invention is based on the unexpected result that HCV-RDRP expressed in *E. coli* was not sufficiently bound to a chelated nickel column to provide significant purification. As disclosed herein, it was found that the enzyme could be purified by affinity binding to a column of chelated cobalt, under conditions described herein. Yield per cell of RDRP was enhanced by incubating *E. coli* cells, after induction of RDRP expression, at a temperature in the range 20° C.–30° C., preferably 26° C.–28° C. Using a two-step purification method described herein, milligram quantities can be obtained of r-HCV-RDRPΔC21-60 oligo His having about 95% purity.

Antibodies against r-HCV-RDRP can be generated by a variety of known techniques for making monoclonal or polyclonal antibodies. Antibodies to r-HCV-RDRP also bind to HCV-RDRP of infected cells, as shown by the discovery that circulating antibodies to HCV-RDRP are detectable in serum of HCV-infected patients, using r-HCV-RDRP as the antibody ligand. A variety of monoclonal antibodies can be selected, having affinity for different epitopes of r-HCV-RDRP, as known in the art. Some antibodies can be inhibitory of enzyme activity. Others can have a modest affinity that facilitates binding to an antibody-affinity column and subsequent elution under conditions that do not inactivate the enzyme.

Mammalian cells are a preferred host cell for certain purposes, particularly for in vitro screening for inhibitors of HCV-RDRP, and also for developing cell lines that can propagate HCV in cell culture. Any of the known cell lines used for transformation can, in principle, be transformed to express r-HCV-RDRP. Preferred cell lines are those of tissue origin known to be infected by HCV or similar viruses, such as flaviviruses. Such cell lines include, for example, the human macrophage cell line U937, human liver-derived hepG2 cells, and the pig kidney cell line PK15. A recently-discovered segment near the 3'-end of HCV-RNA has a predicted cloverleaf-type secondary structure that is a likely site of interaction for a protein or peptide (which may be host-encoded) that regulates HCV-RDRP (Tanaka, T., et al. (1995) *Biochem. Biophys. Res. Commun.* 215:744,749). Such regulation can take the form of altering the template specificity or the catalytic activity of r-HCV-RDRP as well as the wild-type enzyme. Expression of r-HCV-RDRP in cells that normally express the regulatory protein provides an in vivo cell system where expression of r-HCV-RDRP closely approaches the manner of expression in HCV-infected cells. Also, the presence of active HCV-RDRP in a cell can enhance the replication of HCV introduced by infection or by genomic HCV RNA introduced by transfection, by providing a "jump start" for HCV replication. Most importantly, the ability to measure r-HCV-RDRP activity in transformed cells provides an essential key to screening potential inhibitors of HCV-RDRP for their ability to inhibit the enzyme in vivo.

Assay for RNA synthesis by r-HCV-RDRP in vitro has demonstrated that the enzyme can catalyze synthesis of poly(U) using a poly(A) template, and synthesis of RNA, using a globin mRNA template. Both reactions were >90% primer-dependent under the described reaction conditions. The enzyme had no detectable activity in the absence of $Mg^{++}$ and showed maximal activity in the presence of about 20 mM $Mg^{++}$.

A method for screening compounds that have anti-viral activity is provided by testing the effect of various compounds on the RDRP enzyme activity in vitro. The in vitro method includes comparing the amounts of RNA synthesized in the presence and absence of a test compound. An inhibitory effect is indicated if the amount of RNA synthesized is reduced in a reaction where the test compound is present compared to a control reaction where the test compound is absent.

Various assay procedures have been described for measuring HCV-RDRP activity in vitro, as reviewed by Hagedorn, C. et al (2000). A preferred assay process uses the 3'-UTR of HCV RNA as a template without added primer. The reaction rate can be measured by the incorporation of labeled nucleotides into a product of appropriate size.

The stably transfected cell line expressing r-HCV-RDRP is especially useful for carrying out in vivo screening for compounds that inhibit the polymerase in intact mammalian cells. Such inhibitors are likely inhibitors of HCV replication in infected cells. An in vivo test is advantageous since it can screen out cytotoxic compounds, and compounds that cannot enter the cell in sufficient quantity. It also provides the added capability of testing compounds which are precursors of the actual inhibitor but converted to inhibitor by the cells metabolic processes. Examples of precursor inhibitors include nucleoside analogs which must be phosphorylated to be converted to active inhibitor, and compounds having an active group protected by a linkage that undergoes hydrolytic cleavage, intracellularly, to form active inhibitor. Non-nucleoside analogs having the general structure shown are considered attractive candidates for r-HCV-RDRP inhibitors

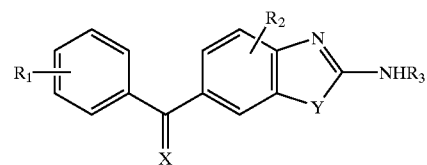

where $R_1$ and $R_2$ are alkyl, amino, hydroxy, alkoxy or halo groups, $R_3$ is an alkyl, aryl, hydroxy or alkoxy group, X is O, $NR_3$, O, $CH_2$ or $CHR_3$. In general, the test cells additionally are transformed with a reporter construct whose expression requires the action of r-HCV-RDRP, or whose expression is amplified by the presence of r-HCV-RDRP. Reporter genes are well known in the art, including, but not limited to luciferase, secreted alkaline phosphatase and the fluorescent green protein, all of which are commercially available. An attractive strategy is to use an antisense gene for the reporter, that is, a version of the reporter gene which expresses an antisense, or (−) strand messenger RNA of the reporter gene. Activity of an RDRP is then required to produce a sense (+) strand in RNA which can be translated to yield active reporter. This system has the advantage that there is no background level of reporter activity in the absence of active HCV-RDRP, if the RDRP is inhibited. An outline for the construction of suitable (−) strand reporter gene is set forth below.

In vivo activity of RDRP can also be measured by replication of a specific RNA template. The RNA template specificity of HCV RDRP is enhanced by the presence of the 3'-non-coding region (3'-NCR) of HCV-RNA which has three stem-loop features of secondary structure that are necessary for infectivity. In addition, the 5'-NCR is reportedly required for negative strand synthesis (see Hagedorn, C. et al (2000)). Therefore expression of a template RNA in a host cell capable of expressing an HCV-RDRP results in specific amplification of the template, measured by strand-specific Northern blotting. Quantitation is provided by incorporation of a labeled nucleotide and measurement of label intensity in the Northern blot. For example, incorporation of a radio-labeled nucleotide is measured by autoradiography. Small molecules can be screened their ability to inhibit the RDRP in vivo based on their ability to inhibit RNA template amplification in the foregoing assay.

Material and Methods

Material—All chemicals were purchased from Fisher and all enzymes from Gibco BRL unless stated otherwise. AmpliTaq was purchased from Perkin-Elmer. All other PCR and ligation components were from Invitrogen. Lysozyme, antibiotics, and pre-stained protein standards were from Sigma. Nucleotides and poly(A) were from Pharmacia. [$^3$H-]UTP was from Dupont NEN. Oligo(U) was a generous gift from E. Ehrenfeld (University of California, Irvine).

EXAMPLE 1

Subcloning of an HCV NS5B Region

PCR-primers for the amplification of an NS5B-region were designed based on the N-terminus as predicted by vaccinia virus expression studies (Lin, C. et al. (1994) supra; Grakoui, A. et al. (1993) supra) and the C-terminus based on the end of the open-reading-frame of the HCV poly protein (Choo, Q-L. et al. (1991) supra). The template was the original prototype HCV (type 1a) clone (obtained from the CDC) (Choo, Q-L. et al. (1989), (1991), supra). Using the following primers, 5'-ATA GCT AGC ATG TCT TAC TCT TGG ACA GG-3' (SEQ ID NO:3) and 5'-ATA GGA TCC TCA TCG GTT GGG GAG GAG G-3' (SEQ ID NO:4), we amplified the NS5B-region with minimum changes at the N-terminus (ASMSY SEQ ID NO:5 instead of SMSY SEQ ID NO:7) and directionally cloned it into pET-11a (Novagen) at NheI and BamHI restriction sites (Maniatis et al. (1982) *Molecular Cloning*, Cold Spring Harbor Laboratory, Plainview, New York). The PCR amplified gene had a NheI site engineered into the 5' end and a BamHI site at the 3' end. This construct results in the synthesis of a recombinant protein with an amino terminal sequence of MASMSY SEQ ID NO: ID NO:6 rather than the SMSY amino terminus of the putative wild-type NS5B protein predicted by vaccinia virus expression studies.

```
             A   S   M   S   Y   S   W   T   (amino acid encoded in primer, SEQ ID NO: 8)
5'-ATA GCT AGC ATG TCT TAC TCT TGG ACA GG-3'   PCR primer directed at the 5' end of
                                                the hepatitis C virus cDNA,
```

```
          A
     C        A
     A        C
     C   =    G
     C   =    G
     A   =    T         This region of the expression vector is
     G        T         removed before inserting PCR product
     A   =    T
     G   =    C
     G   =    C    +26
  pppG   =    C
            TCTAGAAATAATTTTGTTT
            XbaI
                    pet-11a
                             1   2   3   4   5   6   7   8   9  10  11

+50           +61   Met Ala Ser Met Thr Gly Gly Gln Gln Met Gly Arg Gly Ser (SEQ ID NO: 10)
          |             |     ↓
        AACTTTAAGAAGGAGATATACATATG GCT AGC ATG ACT GGT GGA CAG CAA ATG GGT CGC G GA TC (SEQ ID NO: 9)

SD         NdeI     NheI                                          BamHI
                          |
         ┌────────────────┴───────────────────────────────────────────────────┐
                                                                         Cutting site for NheI
                                                                         5'...G▾CTAGC...3'
                                                                         3'...CGATC▴G...5'
        Restriction site in the pET-11A expression vector where
        the 5' end of the PCR amplified NS5B gene was inserted.
```

The PCR reaction was preceded by a 2 min incubation at 94° C., followed by 20 cycles of 1 min 94° C., 2 min 55° C., and 3 min 72° C. (Coy Corporation Tempcycler U). Reactions were completed by keeping the temperature at 72° C. for another 7 min and subsequent cooling to 4° C. Amplified DNA was purified by phenol/chloroform extraction, digested with NheI and BamHI and re-purified using phenol/chloroform extraction and ethanol precipitation.

Insert and vector were ligated overnight at 14.5° C. at an 3:1 ratio (insert:vector) using T4-ligase (Maniatis, supra). Ligated material was used to transform *E. coli* (Top10™ from Invitrogen) using $CaCl_2$ methods. Colonies were selected on ampicillin plates and minipreps of plasmid DNA isolated from single colonies were characterized using restriction enzyme analyses. Plasmid DNA obtained by mini-preparation methods was used to transform BL21 (λDE3) *E. coli* (Novagen), organisms containing plasmid were selected using ampicillin and mini-preparations of plasmid DNA from single colonies were analyzed by restriction enzyme digestion.

Expression, purification and solubilization of HCV RDRP-BL21 (λDE3) *E. coli* containing the pET-11a-NS5B construct described above were grown in overnight cultures (M9ZB media with Carbenicillin) and diluted 1:20 into fresh medium the next morning. Cells were incubated at 37° C. until the culture media reached an OD600 of 0.6. IPTG was added at that time to a final concentration of 1 mM. Expression of the RDRP was followed by SDS-PAGE analysis of whole cells lysed in sample buffer at 90° C.

To solubilize RDRP under non-denaturing conditions cells were harvested 2h after IPTG-induction. RDRP was solubilized by lysing the cells on ice for 20 min in 20 mM Tris pH 7.5, 100 mM KCl, 0.5 mM EDTA, 1 mM DTT, 0.1 % Trition X-100 and 30 μg/ml lysozyme. Samples were sonicated on ice with an 0.5 inch probe (pulse setting) for 5 min (Ultrasonics Inc. W-225, output-setting 7) and centrifuged (19,000 g at 4° C. for 30 min). The insoluble fraction (pellet) obtained from these preparations was enriched with RDRP. Pellets were suspended in SDS-PAGE sample buffer and heated for 10 min at 90° C. and used as RDRP markers for SDS-PAGE gels. However, active enzyme was found in the supernatant, as set forth in the following protocol.

Outline of Solubilization Method for Recombinant RDRP Unmodified by C-terminal Deletion or Addition of Oligo-his.

1. Thaw 5 g of *E. coli* pellet.
2. Resuspend 5 g of pellet in:
   45 ml Lysis buffer
   40 μl 100mM PMSF (plus other protease inhibitors)
   150 μl lysozyme (10 mg/ml)
   Lysis buffer:
     20 mM Tris pH 7.5 (at 4° C.)
     0.5 mM EDTA
     100 mM KCl
     1 mM DTT
     0.1 % Triton X-100 (or 0.1% NP40) 10.0%(v/v) Glycerol
3. Place samples on ice for 20 min, then sonicate for 5 min (pulse mode; setting between 6–7). Mix while sonicating.
4. After sonicating flash freeze the lysate in liquid nitrogen (put the lysate into liquid nitrogen for about 1–2 min).
5. Quickly thaw the lysate at 37° C. water bath.
6. Sonicate the lysate for 1 min.
7. Add an additional 5 ml of lysis buffer per 45 ml of sonicated sample mix.
8. Divide entire sonicated sample into 50 ml fractions (Fisher 50 ml tubes).
9. Centrifuge lysate at 12,500 rpm for 20 min in Beckman J-17 rotor (or 12,500 rpm in a Sorvall SS-34 rotor).
10. Remove supernatants to clean (sterile) 50 ml Fisher tubes and add sterile protein grade glycerol to a final concentration of 10% (for example, 4.44 ml of glycerol/ 40 ml of supernatant). This solution is stored at 4° C. and used as starting material for the purification of enzymatically active HCV RDRP.

Further purification is accomplished by employing the following steps, either singly or in combination.

Soluble proteins from lysate of *E. coli* expressing recombinant
HCV RDRP
(10,000 × g supernatant)
↓
45% ammonium sulfate precipitated proteins
(subsequently dialyzed in Tris-pH 7.5
with 10% glycerol and 1 mM DTT)
↓
DEAE anion exchange chromatography
(starting material applied at pH 8.5 - Tris buffer,
wash step with same buffer and enzyme
is eluted with a 0–0.5 M NaCl gradient)
↓
Phosphocellulose chromatography
(concentrated DEAE fractions containing enzyme
are diluted to decrease salt concentration and change
pH to 8.0 (Tris/HCl) before applying samples to column,
wash step, and elution with a 0–0.5 M NaCl gradient)
↓
FPLC gel filtration chromatography
(Superose 12 HR 10/30 - Pharmacia)
(starting material is concentrated, buffer changed
to 150 mM NaCl with Tris pH 8.0 and applied in
a 200 μl volume with a flow rate of 0.3 ml/min)
↓
Recombinant HCV RDRP for enzyme assays
(stored in aliquots at −70° C. with Tris-pH 8.0,
100 mM NaCl, 20% glycerol, 0.1% NP-40, & 1 mM DTT)

As in all protein purification procedures, one can modify buffers, pH and other conditions to further optimize the purification of HCV RDRP. An additional final purification step (or substitution for the FPLC gel filtration step) is a Mono-S cation exchange chromatography step at pH 6.0 with a MES buffer (the isoelectric point of the enzyme is approximately 8.8). All purification steps are monitored for enzyme activity using RDRP assay, total protein, and analyzed by SDS-PAGE.

EXAMPLE 2

Modifications of NS5B Region

An NS5B clone of HCV type 1b was modified essentially as described in Example 1 to add an N-terminal MS dipeptide to permit expression of RDRP in a transformed host cell. The nucleotide and amino acid sequences of the type 1b NS5B clone are given in SEQ ID NO: 11 and NO: 12, respectively. An annotated amino acid sequence is given in Table 1 using single letter amino acid code. The amino acids highlighted by stippling are those which differ from corresponding sites of the type 1a RDRP of SEQ ID NO:2. For expression and purification of any RDRP in soluble form, from 21 to 60 C-terminal amino acids can be deleted. Ease of purification is enhanced by substituting an oligo-his tag for the deleted C-terminal amino acids, using methods described herein. Preferred oligo-his tags have the sequence $LEH_6$, $A_nSH_6$, or $G_nSH_6$, where n=1,2,3,4, or ,5. The general notation used herein for an RDRP having a C-terminal deletion and oligo-his substitution is RDRP/ CΔ21-H.

Enzyme properties of the RDRP of a given HCV isolate can be enhanced by incorporating amino acid replacements at designated positions in the RDRP amino acid sequence. Properties which can be enhanced by such replacements include enzyme activity, template specificity, processivity, stability in vitro or in vivo, and the like. One or more of the following amino acids are the most preferred for optimal enzyme properties: enzymic activity: R at position 67, K at position 116, E at 133, S at 220, A at 340, and S at 302. Also preferred, but of lower priority, are one or more of the following amino acids: R at 533, K at 100, T at 209, L at 49, N at 233, R at 512 and S at 551. (Amino acid positions are numbered as in Table 1). The foregoing modifications can be combined in any desired combination and can also be combined to enhance the enzyme properties of a RDRP whose natural sequence contains one or more of the preferred amino acids. In Table 1, the amino acids selected for replacement are set in boldface type and underlined. An essential GDD sequence, common to most RDRP enzymes, is set in boldface type but not underlined. Although Table 1 illustrates amino acid replacements for a type 1*b* NS5B isolate, the same amino acids can be used to replace the existing amino acid at the same locus, for any NS5B isolate, regardless of the strain.

The hydrophobic tail which renders the isolated RDRP insoluble in aqueous media functions in vivo to anchor the polymerase to the cell membrane. In order to assay the activity of the recombinant RDRP in transformed eukaryotic cells, the full length protein is preferred. (The segment underlined in Table 1, positions 573–593 is not deleted). In addition to the described amino acid replacements previously described, certain amino acid replacements within the C-terminal anchoring domain can be made in order to enhance in vivo enzyme properties. Preferred amino acid replacements include one or more of the following: W at 575, F at 576, A at 582, and K at 583. (In all cases, amino acid positions are numbered as in Table 1).

All amino acid replacements are accomplished by modifying the NS5B coding, working with the DNA copy thereof. Coding modifications are made by site directed mutagenesis to change an existing codon to a known codon for the desired amino acid using known methods. A commercially available process is employed herein, the Stratagene Quick Change site directed mutagenesis system. Examples of specific primers include the following:

Examples of Mutagenesis Primers
(for use with Stratagene Quikchange Site-Directed Mutagenesis Sytem)

```
Q67 → R
"forward" primer: 5'-CTG GAC GAT CAC TAC AGG GAC GTG CTC AAG GAG-3' (SEQ ID NO:13)
"reverse" primer: 5'-CTC CTT GAG CAC GTC CCT GTA GTG ATC GTC CAG-3' (SEQ ID NO:14)

A133 → E
"forward" primer: 5'-CTG CTG GAA GAC ACT GAA ACA CCA ATT GAC ACC-3' (SEQ ID NO:15)
"reverse" primer: 5'-GGT GTC AAT TGG TGT TTC AGT GTC TTC CAG CAG-3' (SEQ ID NO:16)

R116 → K
"forward" primer: 5'-CGG AAC CTA TCC AGC AAG GCC GTT AAC CAC ATC-3' (SEQ ID NO:17)
"reverse" primer: 5'-GAT GTG GTT AAC GGC CTT GCT GGA TAG GTT CCG-3' (SEQ ID NO:18)

A220 → S
"forward" primer: 5'-GAA ATG CCC TAT GGG CTT TTC ATA TGA CAC CCG CTG TTT CG-3'
                                                    (SEQ ID NO:19)
"reverse" primer: 5'-CGA AAC AGC GGG TGT CAT ATG AAA AGC CCA TAG GGC ATT TC-3'
                                                    (SEQ ID NO:20)

S233 → N
"forward" primer: 5'-CTC AAC AGT CAC AGA GAA TGA CAT CCG TGT TGA GG-3'
                                                    (SEQ ID NO:21)
"reverse" primer: 5'-CCT CAA CAG GGA TGT CAT TCT CTG TGA CTG TTG AG-3'
                                                    (SEQ ID NO:22)
```

Expression and purification of C-terminal-deleted, oligohis tagged RDRP was carried out according to the following protocol: BL21 DE3 cells were transformed with 5Bpol expression plasmid DNA as described and plated on LB agar containing 100 μg/ml carbenicillin. An overnight culture of at least 200 ml terrific broth (TB) containing 300 μg/ml carbenicillin was inoculated with a single colony from the transformation plate. TB contains 12 g/l Bactotryptone, 24 g/l yeast extract, 4 ml/l glycerol, 2–31 g/l KH $_2PO_4$ and 12.54 g/l $K_2HPO_4$. The culture (0.5 ml) was used to inoculate 50 ml of TB containing 500 μg/ml carbenicillin which was then incubated at 37° while mixing at 250 rpm (New Brunswick Sci. Incubator) until the culture medium became cloudy. Cells were harvested in an IEC centrifuge at 7000 RPM for 10 min. The cell pellet was resuspended in 5–10 ml fresh TB for starter culture. Carbenicillin was added to the 2L flasks of TB to 500 ug/ml. A 1 ml sample of the TB media was taken from one of the 2L flasks before inoculating for a density zero. 2L flasks of TB containing 500 μg/ml carbonicillin were inoculated with 1 ml of starter culture, and incubated at 37° C. and 250 rpm, as described supra. Cell. growth was monitored by measuring optical density at 600 nm. At a density of about 0.4 the temperature was reduced to 27° C. A reduced temperature during induction of recombinant protein synthesis increases enzyme yield. The exact reduced temperature is not critical and temperatures in the range from 24° C.–30° C. are useful. A preferred temperature range is from 26° C.–28° C. An uninduced (no IPTG) sample of *E. coli* cells was removed for control SDS-PAGE analysis. At $OD_{600}$ of 0.5 IPTG was added to each flask to produce a final concentration of 1 mM to induce expression of rHCV-RDRP. Cells were incubated at 27° C. and 250 rpm for 4–8 more hours. Samples of cells at different induction times were saved for SDS-PAGE analysis. Cells were harvested by centrifugation at 5000 rpm for 10 minutes at 4° C. in 400 ml preweighed bottles in a GSA3 rotor (Sorvall RC5C centrifuge). Cell pellets were frozen at −80° C. or used directly in purifications as described below.

Solubilization/Purification of recombinant NS5B polymerase (CΔ21 oligo-his)

Approximately 4 g (wet weight) aliquots of *E. coli* cell paste were lysed by sonication or by a French press in lysis buffer containing 50 mM HEPES pH 8.0,
400 mM NaCl,
and 10% to 50% glycerol,
1 mM PMSF (freshly prepared)
10 μg/ul Benzamidine, aprotinin, Leupeptin, and Pepstatin A
and 1 % NP40. Cells were mixed with lysis buffer, 10 ml/g of cell paste, resuspended by repeated pipetting. For sonication, each tube of cells (approximately 40 ml) was sonicated in a Heat Systems Ultrasonics Inc. model W-225 sonicator for 5×30 sec in a rotation so that each tube was sonicated for 30 sec and the cycle was repeated five times. Sonication was done in this manner to prevent excessive heating of the samples. A large sonication probe (0.5 cm diameter) was used on the pulse mode, 60%, and power setting 7. The lysate was transferred to an open-ended centrifuge tube, balanced, and centrifuged at 12,000 rpm for 15 minutes in a JA-17 rotor (Beckman J2-21M) to pellet particulate material. The supernatant was recovered and kept on ice in clean 50 ml Corning tubes. The supernatant was diluted 1:1 with lysis buffer containing no NaCl. The diluted lysate served as starting material for the metal chelated column with a final NaCl concentration of 200 mM. A sample of the starting material was saved for SDS-PAGE and protein analysis. Metal chelation chromatography was carried out on a $Co^{++}$-chelated column (Talon™, ClonTech) having a 1 ml bed volume. The column was prepared by three steps, passing through $1^{st}$—10 ml 20 mM MES pH 5.0 with 1M NaCl (for cleaning a previously used column)
$2^{nd}$—5ml deionized $H_2O$ (wash step)
$3^{rd}$—5 ml binding buffer (equilibration step)
Binding buffer was composed of
50 mM HEPES pH 8.0,
200 mM NaCl,
10% glycerol,
0.5% NP40,
plus protease inhibitors at 50% of the concentrations present in the lysis buffer.

Diluted lysate was then passed through the column followed by a wash with 10 ml binding buffer, then a wash with 5 ml binding buffer+3mM imidazole, followed by elution with 9 ml binding buffer +100 mM imidazole. Fractions were collected in small (0.5–1 ml) aliquots and analyzed for protein. To further purify fractions containing recombinant NS5B polymerase a FPLC heparin Sepharose Hi-trap column (Pharmacia, Piscataway, N.J.) was used.

Buffer A
20 mM HEPES pH 7.3
100 mM NaCl
10% glycerol
5 0. 1% NP40
1 mM DTT
(note: other detergents can be used and the concentrations varied)
Buffer B—same as buffer A except 2M NaCl.

The Heparin Sepharose FPLC column (1 ml) was prepared by washing with 10 ml buffer B then 10 ml buffer A at a flow rate of 1 ml per min. Purified protein obtained from the metal chelating column (e.g. Talon™ $Co^{++}$ resin) was diluted to reduce the salt concentration during the binding step to the FPLC column (e.g. 1:2.5 with buffer A). After loading the protein on the column, and a 15 ml wash w/buffer A, the column was eluted with a 60 ml gradient from 0–50% buffer B, followed by a
30 ml gradient from 50–100% buffer B, a
10 ml wash w/100% buffer B and a
10 ml wash w/buffer A.

Figure 9:
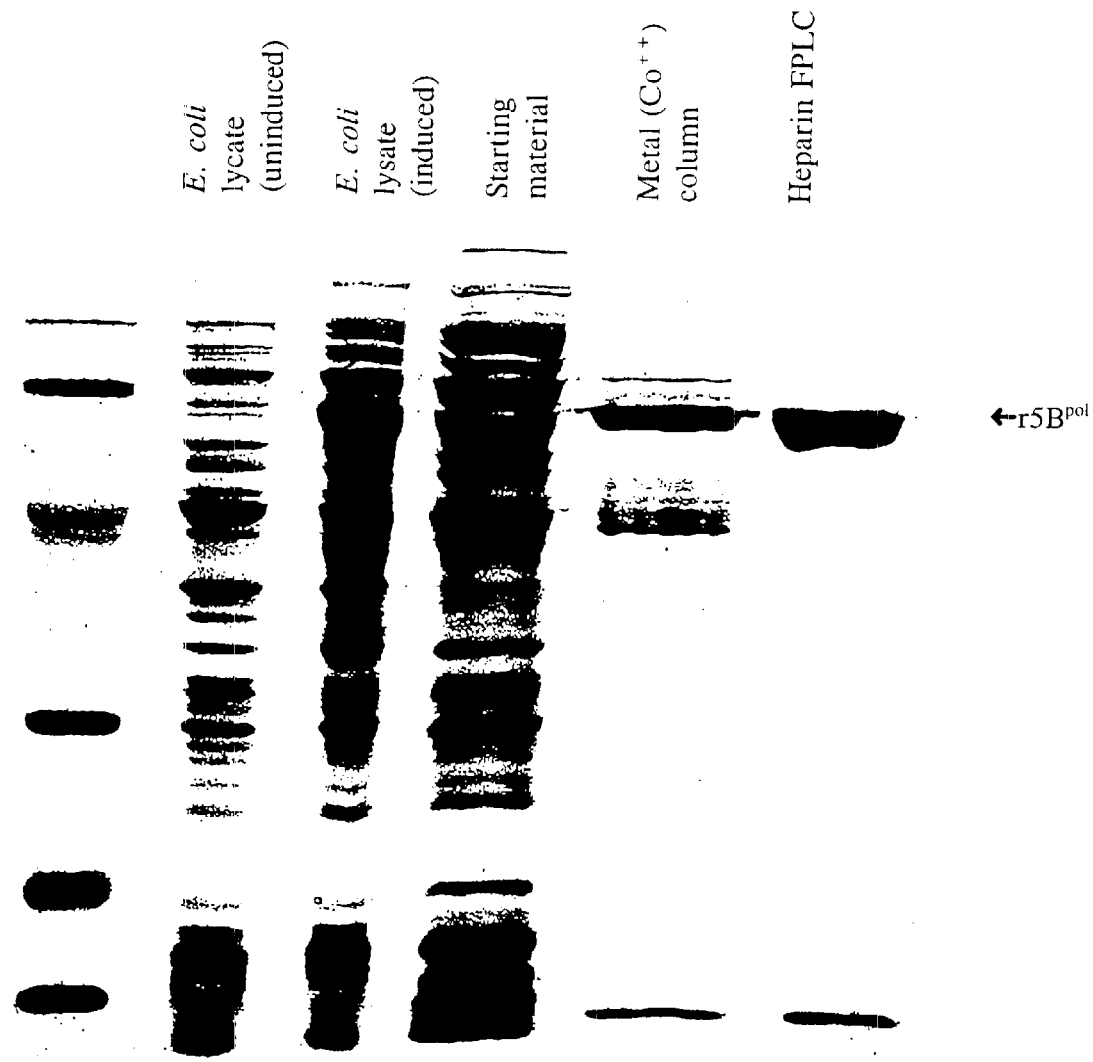
FIG. 9 is an SDS-PAGE analysis of proteins sampled at various stages of purification, (Example 2).

Peak fractions of 1 ml were collected. Fractions were analyzed by SDS-PAGE: rHCV-RDRP eluted at ~27.5% buffer B or ~550 mM NaCl. Based on SDS-PAGE analysis (FIG. 9) rHCV-RDRP was obtained at least 95% pure. A 3L culture of *E. coli* provided 10.63 (net weight) of centrifuge-collected cells which, after lysis, yielded 95 ml lysate. Yield from 95 ml lysate was 3.14 mg RDRP, as shown in Table 3, purity was at least 95 %, as shown in FIG. 9.

Rabbit anti-HCV RDRP serum: RDRP solubilized from the pellet fraction as described above or eluted from Fast Protein Liquid Chromatography was separated by preparative SDS-PAGE and used to immunize rabbits. Animals were immunized at 4–5 week intervals as described in detail previously. (Harlow, E. and D. Lane (1988) *Antibodies: A laboratory manual*, Cold Spring Harbor Laboratory, pp. 553–611.)

Immunoblotting analysis: Immunoblots were performed using previously described methods with the modification that secondary HRP conjugated antibodies were used with the enhanced chemiluminescent system (ECL, Amersham). When rabbit serum was the primary antibody, the secondary antibody was anti-rabbit immunoglobulin. When human serum was screened the secondary antibody was anti-human immunoglobulin. Serum from patients with documented chronic hepatitis C infections was provided by Dr. Michael Beach of the Centers for Disease Control and Prevention (Atlanta).

Assay conditions for r-HCV-RDRP activity: The preferred conditions for assaying RDRP activity are described. The alternative conditions are operative, and designated as alternatives, in parentheses. Incubations were carried out 20 or 50 μl in final volumes that contain: 20–50 mM HEPES-pH 8.0 (alternative is 20 mM Tris-HCl;pH 7.5); 1.5–5 mM $MnCl_2$; 100 mM ammonium acetate; 1–4 mM dithiothreitol (DDT), 500 μM each ATP, CTP, and GTP (alternative: 500 μM GTP and 250 μM each ATP and CTP); 10 μM UTP; 1–20 μCi of [α-$^{33}$P]UTP (alternative is to use [α-$^{32}$P]UTP or [$^3$H]UTP), 10–20 U of RNasin; and rHCV-RDRP protein. Templates: 500–1000 ng of a preferred heteropolymeric template (e.g., either a 98 nt 3'-end of HCV genomic RNA or HCV RNA that included both the 5' and 3' ends of genomic or negative stranded HCV RNA) per 50 μl incubation; (as an alternative template, poly(A)/oligo(U) on either 20 μg/ml poly(A)$_{460-600}$, and 10 μg/ml oligo (U)$_{5-25}$ (or 0.8 μg of 10:1 mix of poly(A)/oligo(U) per 50 μl incubation can be employed). If the enzyme preparation is not >90–95 % pure include 50 μg/ml of actinomycin D. Incubations are for 15–120 min at 30° C. (or 22° C.). Note: stop incubations by adding 100 mM EDTA and then process for trichloroacetic acid (TCA) precipitation.

Labeled nucleotides incorporated into RNA are precipitated by TCA. The precipitates are collected, washed and counted, e.g. in a scintillation counter to measure the quantity of RNA synthesized in the enzyme reaction. Incubations were at 30° C. for 30–60 min, [$^3$H]poly(U) was precipitated with TCA in the presence of carrier DNA and collected on Whatman GF/C filters. Filters were washed with 0.1 M sodium pyrophosphate/1 N Hydrochloric acid and 95 % ethanol, respectively. [$^3$H]poly(U) was quantitated by liquid scintillation spectrometry (LKB 1218 RackBeta). The synthesized RNA can also be analyzed by gel electrophoresis to determine the size of the synthesized RNA chains. For gel analysis the reaction mixture is inactivated with 100 μl of proteinase K buffer; digested with proteinase K, processed and the RNA products are analyzed by formaldehyde/agarose gel electrophoresis or 6% denaturing polyacrylamide-7 M urea gel electrophoresis.

EXAMPLE 3

Stable Transfection of Baby Hamster Kidney (BHK) Cells Using Cationic Lipid

Day 1 (Afternoon)

Split the BHK cells into 6 well plates aiming for 50% confluence for transfection Day 2 (After 4 p.m.)

Prepare the following solutions in sterile tubes:

(A) 50 μl miniprep DNA +50 μl media without serum (DMEM/F12) (2 each)

(B) 6.25 μl cationic lipid (Gene Porter) (Trademark, Gene Therapy Systems, Inc. San Diego, Calif.) +93.75 μl media (C) 12.5 μl Gene Porter+87.5 μl media (D) 6.25 μl Gene Porter+193.75 μl media (mock transfection)

(E) 12.5 μl Gene Porter+187.5 μl media (mock transfection)

Gently mix A&B and A&C and let the DNA and cationic lipid react for 15 minutes at room temperature. During this time, wash the cell twice with 2 mls of DMEM/F12. Add 1.8 mls of DMEM/F12 to the DNA/cationic lipid complex and add it to the cells with gentle swirling. Leave the cells in the incubator overnight.

Day 3 (9 a.m.)

Remove the DNA/Gene Porter and add 3 mls of media+ serum to the cells. Incubate the cells for 30–48 hours. Split the cell 1:20, 1:50 and 1:100 into 10 cm dishes in 10 mls of media+serum containing 600 μg/ml geneticin. Allow 3–7 days for selection and 10–14 days for colony formation. The same protocol can be adapted to employ Starburst Dendrimer (Life Technologies, Gaithersburg, Md.) instead of Gene Porter, to improve transfection efficiency.

After selection, ring clone colonies onto 24 well plates and assay media from confluent wells for RDRP activity. Maintain cells in 600 μg/ml geneticin.

EXAMPLE 4

Use of Transfected Cells Expressing HCV RDRP to Identify Compounds that Enter Intact Cells and Inhibit HCV RDRP The most direct approach to determining the effect of potential inhibitors of HCV RDRP in transformed cells is to directly measure RDRP activity in cell extracts after cells have been incubated with compounds and washed extensively. This can be done using the RDRP assay described herein (with a HCV template) and requires no other new development except the cell-line. In brief, cells are incubated under conditions that maximally express active enzyme and in sufficient quantities for subsequent enzyme assays. Test compounds are added to incubation media, then cells are removed at the desired time and extensively washed to remove extracellular go test compounds. Extracts of the cells are prepared for RDRP assays following the general methods described herein. This approach is relatively rapid and requires only moderate changes in current methods (new cell-lines). By measuring this activity recovered at different times following exposure to the inhibitor one can determine how rapidly the inhibition occurs in cells. Care must be taken to avoid contamination of cell lysates with a compound that does not enter cells but contaminates lysates during their preparation. The test includes controls to insure that washing procedures are optimal. The major advantage of this system is that compounds that may require labor intensive modifications (phosphorylation of nucleosides) for testing with purified RDRP are rapidly screened.

A more rapid screening can be achieved by transiently transfecting cells that have been incubated with potential inhibitors with a plasmid engineered to express an HCV RNA template that also encodes an easily measured reporter molecule (such as secreted alkaline phosphatase or luciferase). Such a system measures HCV RDRP activity in intact cells (concentrations of inhibitions would not be diluted by lysing cells, etc). Cells in which RDRP activity is inhibited can be rapidly screened, so that large numbers of candidate inhibitors can be screened rapidly.

A reporter system has been devised whereby activity of r-HCV-RDRP expressed in a host cell is required for expression of a reporter gene. The host cell is transfected with a construct designed to carry the reporter coding sequence in antisense form in a structure that models the HCV replicative intermediate, when expressed as mRNA. The mRNA has, starting from the 5' end, a cap site, the reporter coding region in the antisense, (−) strand, form, an HCV internal ribosome entry site (IRES) element, also in (−) strand form, a ribozyme sequence in (+) strand form, and a polyadenylation site in (+) strand form. Such an mRNA, if translated, would give rise to a nonsense protein, encoded from the (−) strand of the reporter gene. By accepted convention in the art, an "RNA(+) strand encodes a "sense" message that is translatable to yield the desired encoded protein. An RNA(−) strand has the complementary sequence to the (+) strand, is sometimes referred to as the "antisense" strand and is not translatable to yield the desired protein. However, if the complementary strand is synthesized by r-HCV-RDRP, the coding sequence of the (+) strand is translatable as the reporter protein (e.g., luciferase, fluorescent green protein, secreted alkaline phosphatase, etc.). The complement produced by RDRP lacks a capped 5' end, since the complement synthesis by RDRP occurs in the cytoplasm and capping occurs in the host cell nucleus. However, the presence of the HCV-IRES element allows cap-independent translation. (The IRES element will be situated 5' to the (+) strand coding sequence in the complementary strand). The function of the ribozyme motif is to remove the polyA tail from the 3' end of the (−) strand, and incidentally to remove itself as well, prior to complementary strand synthesis by RDRP. A suitable ribozyme motif is provided, for example, by the R₂89$_{CC}$ ribozyme of hepatitis delta virus. As transcribed from an integrated DNA, the reporter in RNA can be diagramed as

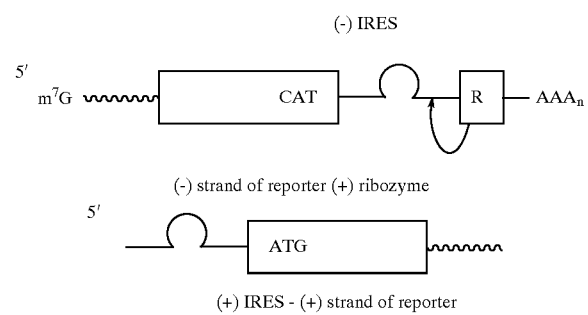

Additions to the foregoing structure include providing a sequence of the HCV 3' untranslated region, which provides a secondary structure that can regulate or enhance r-HCV-RDRP activity. The action of r-HCV-RDRP permits expression of the reporter gene, such that a readily identifiable reaction product such as fluorescence, chemiluminescence or dye generation reaction. The presence of such reaction products indirectly indicates the activity of the r-HCV-RDRP expressed in the host cell and therefore provides a means for observing the effects of a test compound on r-HCV-RDRP activity, in vivo. Inhibitors of in vivo r-HCV-RDRP activity are potential anti-viral agents against HCV. Suitable reporter genes are known in the art, including, for example, luciferase, secreted alkaline phosphatase, chloramphenicol acetyl transferase or fluorescent green protein. Assays for reporter activity are well-known, depending on properties of the reporter and can also include immunoassays such as ELISA.

Figure 8:
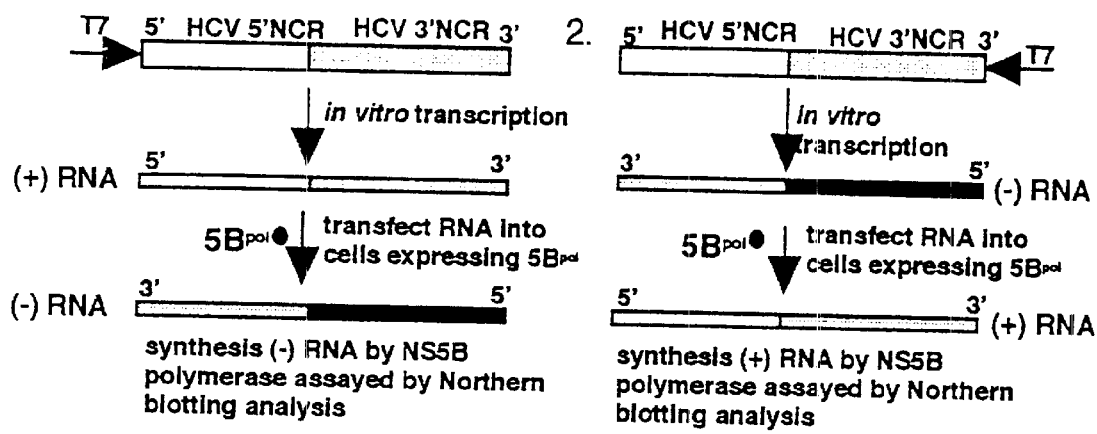
FIG. 8 is a diagram showing steps of a method for detecting and measuring HCV-RDRP activity in vivo in mammalian cells, by measurement of specific template amplification. The left-hand panel shows the steps of preparing a (+)RNA template for amplification and assay by a strand-specific assay. The right-hand panel shows the steps of preparing a (−)RNA template for amplification and assay in like fashion.

A more direct assay is based on measurement of amplification of a specific template by r-HCV-RDRP. The presence and amount of amplified template is measured by strand-specific Northern blotting. Other means for strand-specific assay can be employed, including strand-specific amplification by polymerase chain reaction. The method is diagramed in FIG. 8. Two types of specific template are employed. In the first of these, a DNA having the sequence of the 5'-NCR and 3'-NCR of HCV-RNA is combined with a T7 promoter adjacent the 5' end. After PCR amplification, the DNA is transcribed in vitro to produce (+)RNA having 5'- and 3'-NCR segments of HCV-RNA. As previously noted, these segments contribute to template specificity of HCV-RDRP. In the second type of specific template, the same DNA construct is provided with a T7 promoter adjacent the HCV-3'-NCR (FIG. 8, right hand panel). In vitro transcription yields (−)RNA having 5'- and 3'-NCR segments of HCV-RNA. Cells expressing r-HCV-RDRP are then transfected with either the (+)RNA or the (−)RNA. RNA transfection can be carried out by a variety of processes known in the art. A presently preferred method employs a cationic lipid transfection reagent such as the GenePORTER™ reagent available from Gene Therapy Systems, Inc., San Diego, Calif. In general, the protocol provided by the manufacturer can be followed. The day before transfection, cells are plated so that they will be 60–90% confluent on the day of transfection. The transfecting RNA is diluted with serum-free medium 10 ug RNA in a 1 ml transfection volume for transfecting cells grown in a standard T-25cm$^2$ flask. The cationic lipid reagent, 10–30 ul, is also diluted in 1 ml of serum-free medium. The reagent and the RNA are combined and incubated for 10–45 minutes, 45 minutes being preferred. The culture medium is aspirated from the cells and the RNA-cationic lipid mixture added, followed by incubation at 36° C. for 3–5 hours. One volume of medium containing 20% FCS is then added and incubation is continued overnight under 5–10% $CO_2$ at 37° C. Twentyfour hours post transfection, fresh growth medium can be added as needed, followed by assay of RDRP activity. Other suitable transfection reagents are known in the art, such as LipofectACE (Trademark, Gibco/BRL, Gaithersburg, Md.). The activity of the intracellular RDRP results in amplification of copies of opposite polarity to the transfecting template, which are then measured by a strand-specific assay such as Northern blotting. Other suitable stand-specific assays include the use of label-tagged oligonucleotide probes specific for a given strand and PCR-based amplification methods such as RT-PCR. Any of the foregoing methods can be applied to measure the amount of an RNA template or its complement produced in the transfected cell. Detection and measurement of specific RNA synthesis is accomplished by incorporating a labeled nucleotide precursor into newly synthesized RNA. For example, incorporation of a radio-labeled nucleotide is measured by autoradiography. Small molecules can be screened for their ability to inhibit the RDRP in vivo based on their ability to inhibit RNA template amplification in the foregoing assay.

While the invention has been disclosed in detail with respect to certain specific embodiments and examples, it will be understood that further embodiments, examples and modifications made according to one or more of the teachings, principles and results disclosed herein, combined with knowledge in the art as applied by a person of ordinary skill therein all fall within the scope of the invention.

TABLE I

Modified NS54B pol genotype 1b; Expression in *E. coli* with pET21 or mammalian cells using other vectors (SEQ ID NO;12)

| | | | | | |
|---|---|---|---|---|---|
| 1 | MA | SMSY?WTGAL | ?TPCAAEEQK | LPINALSNSL | LRHHN?VY?T TSRSA?QRQK |
| 53 | | SMSY?WTGAL | ?TPCAAEEQK | LPINALSNSL | LRHHN?VY?T TSRSA?QRQK |
| 103 | | FGYGAKDVR? | ???RAV?HI? | SVWKDLLED? | ATPIDTTIMA KNEVFCVQPE |
| 153 | | KGGRKPARLI | VFPDLGVRVC | EKMALYDVVS | ?LP?AVMGSS YGFQYSPGQR |
| 203 | | VEFLV?AWKS | KK?PMGFAYD | TRCFDSTVTE | SDIR?EE?TY QCCDL?P?AR |
| 253 | | QAI?SLTERL | Y?GGPLTNS? | GQNCGYRRCR | ASGVLTTSCG NTLTCY?KAT |
| 303 | | AACRAA?LQD | CTMLVCGDDL | VVICESAG?Q | EDAASLRVFT EAMTRYSAPP |
| 353 | | GDPPQPEYDL | ELITSCSSNV | SVAHD??GKR | VYYLTRDPTT PLARAAWETA |
| 403 | | RHTPVNSWLG | NIIM?APTLW | ARMILMTHFF | S?L?A??QLE ?ALDC?IYGA |
| 453 | | CYSIEPLDLP | ?IIQRLHGLS | AFSLHSYSPG | EINRVA?CLR KLGVPPLR?W |
| 503 | | RHRARSVRAK | LLS?GGRAA? | CGKYLFNWAV | KTKLKLTPI? AA?QLDLSGW |
| 553 | | ?TAGYSGGDI | YHS?S?ARPR | WEMWCLLLLS | VGVGIYLLPN R |

TABLE 2

| Alternative NS5B pol mutagenesis template; Expression in *E. coli* with pET21 or mammalian cells using other vectors (SEQ ID NO:23) |
|---|
| 1 MA SMSYTWTGAL ITPCAAEEQK LPINALSNSL LRHHNMVYAT TSRSASLRQK |
| 53 KVTFDRLQVL DDHYQDVLKE MKAKASTVKA KLLSVEEACK LTPPHSAKSK |
| 103 FGYGAKDVRN LSSRAVNHIH SVWKDLLEDT ETPIDTTIMA KNEVFCVQPE |
| 153 KGGRKPARLI VFPDLGVRVC EKMALYDVVS TLPQVVMGSS YGFQYSPGQR |
| 203 VEFLVNTWKS KKCPMGFSYD TRCFDSTVTE NDIRVEESIY QCCDLAPEAR |
| 253 QAIKSLTERL YIGGPLTNSK GQNCGYRRCR ASGVLTTSCG NTLTCYLKAS |
| 303 AACRAAKLQD CTMLVNGDDL VVICESAGTQ EDAASLRVFT EAMTRYSAPP |
| 353 GDFPQPEYDL ELITSCSSNV SVAHDASGKR VVYLTRDFTT PLARAAWETA |
| 403 RHTPVNSWLG NIIMYAPTLW ARMILMTHFF SILLAQEQLE KALDCQIYGA |
| 453 CYSIEPLDLP QIIERLHGLS AFSLHSYSFG EINRVASCLR KLCVPPLRVW |
| 503 RHRARSVRAK LLSQGGRAAT CGKYLFNWAV KTKLKLTPIP AASQLDLSGW |
| 553 *VTAGYSGGDI YHSLSRARPR WFMWCLLLLS VGVGIYLLPN R* |

TABLE 3

| | Volume | Protein Conc. mg/ml | Protein Total mg | Yield mg RDRP | % purity | % Recovery of soluble RDRP |
|---|---|---|---|---|---|---|
| Lysate (S.M.) | 95 ml | .122 | 11.4 | | | |
| $Co^{++}$ chromatography | 27 ml | 0.304 | 8.21 | 6.0 est. | 83% | 65.2% |
| Heparin-Sepharose chromatography | 10 ml | 0.32 | 3.20 | 3.14 | 98% | 34.1% |

What is claimed is:

1. An isolated and purified recombinant hepatitis C virus RNA-dependent RNA polymerase (r-HCV-RDRP) having an amino acid sequence encoded by the isolated NS5B coding sequence of SEQ ID NO:12 modified to encode one or more of the following amino acids substituted for the corresponding amino acid encoded by the isolated NS5B sequence: Ser or Glu at amino acid position 21; Arg or Lys at amino acid position 67, Lys at amino acid position 100, Lys at amino acid position 116, Glu or Val at amino acid position 133, Ser at amino acid position 220, Ser at amino acid 302, or Ala at amino acid position 340, said r-HCV-RDRP having in vitro RDRP activity.

2. The r-HCV-RDRP of claim 1 further comprising a carboxy-terminal deletion of from 18 to 57 amino acids.

3. The r-HCV-RDRP of claim 2 further comprising a sequence selected from the group LeuGlu(His)$_6$, (Ala)$_n$Ser(His)$_6$ or (Gly)$_n$Ser(His)$_6$ when n is 1–5, substituted for said deletion.

4. The r-HCV-RDRP of claim 3 having a carboxy-terminal deletion of 55 amino acids and the sequence LeuGlu(His)$_6$ substituted for said deletion.

5. A method of enhancing enzyme properties of an isolated recombinant hepatitis C virus RNA-dependent RNA polymerase (r-HCV-RDRP) having an amino acid sequence encoded by the isolated NS5B coding sequence of SEQ ID NO:12, comprising modifying the amino acid sequence of said r-HCV-RDRP by substituting at the designated amino acid position one or more of the following amino acids: Ser or Glu at amino acid position 21; Arg or Lys at amino acid position 67, Lys at amino acid position 100, Lys at amino acid position 116, Glu or Val at amino acid position 133, Ser at amino acid position 220, Ser at amino acid position 302, or Ala at amino acid position 340, whereby enzyme properties of the isolated r-HCV-RDRP are enhanced.

* * * * *

UNITED STATES PATENT AND TRADEMARK OFFICE
CERTIFICATE OF CORRECTION

PATENT NO. : 6,461,845 B1
DATED : October 8, 2002
INVENTOR(S) : Hagedorn

It is certified that error appears in the above-identified patent and that said Letters Patent is hereby corrected as shown below:

Title page,
Item [56], OTHER PUBLICATIONS, "Tanaka reference:" insert a space between "3'" and "Terminus"

Column 2,
Line 63, delete "RN" and replace with -- RNA --.

Column 6,
Line 25, delete "SB" and replace with -- 5B --.

Column 8,
Line 35, delete "al" and replace with -- at --.

Column 11,
Line 18, delete "single4letter" and replace with -- single-letter --.

Column 14,
Line 31, delete the second occurrence of "ID NO:".

Columns 13 and 14,
Approximately 6 lines from the bottom, above "BamHI", delete
"G GA TC(SEQ ID NO:9)" and replace with -- GGA TCC (SEQ ID NO:9) --.

Column 18,
Line 39, delete "KH $_2$PO$_4$" and replace with -- KH$_2$PO$_4$ --.

Column 21,
Line 61, delete "go".

Column 24,
Table I, second line of the amino acid sequence from residue 53 to 102, replace "SMSY WTGAL TPCAAEEQK LPINALSNSL LRHN VY T TSRSA QRQK"
   with --KVTFDRLQVL D HYQDVLKE KA AS VKA LLSVEEAC LTPPHSARSK--;

Fifth line of the amino acid sequence from residue 233 to 242, replace "SDIRVEESTY" with -- SDIRVEESIY --.

UNITED STATES PATENT AND TRADEMARK OFFICE
CERTIFICATE OF CORRECTION

PATENT NO. : 6,461,845 B1
DATED : October 8, 2002
INVENTOR(S) : Hagedorn

It is certified that error appears in the above-identified patent and that said Letters Patent is hereby corrected as shown below:

Column 25,
Table 2, eighth line of the amino acid sequence from residue 353 to 362, replace "GDFPQPEYDL" with -- GDPPQPEYDL -- and from residue 383 to 392, replace "VYYLYTRDFTT" with -- VYYLTRDPTT --;

Tenth line of the amino acid sequence from residue 473 to 482, replace "AFSLHSYSFG" with -- AFSLHSYSPG --.

Signed and Sealed this

Eighteenth Day of February, 2003

JAMES E. ROGAN
*Director of the United States Patent and Trademark Office*

SEQUENCE LISTING

```
<160> NUMBER OF SEQ ID NOS: 23

<210> SEQ ID NO 1
<211> LENGTH: 1788
<212> TYPE: DNA
<213> ORGANISM: Hepatitis C virus
<220> FEATURE:
<221> NAME/KEY: CDS
<222> LOCATION: (1)..(1782)

<400> SEQUENCE: 1 atg gct agc atg tct tac tct tgg aca ggc gca ctc gtc acc ccg tgc       48
Met Ala Ser Met Ser Tyr Ser Trp Thr Gly Ala Leu Val Thr Pro Cys
  1               5                  10                  15 gcc gcg gaa gaa cag aaa ctg ccc atc aat gca cta agc aac tcg ttg       96
Ala Ala Glu Glu Gln Lys Leu Pro Ile Asn Ala Leu Ser Asn Ser Leu
             20                  25                  30 cta cgt cac cac aat ttg gtg tat tcc acc acc tca cgc agt gct tgc      144
```

-continued

```
Leu Arg His His Asn Leu Val Tyr Ser Thr Thr Ser Arg Ser Ala Cys
        35                  40                  45 caa agg cag aag aaa gtc aca ttt gac aga ctg caa gtt ctg gac agc      192
Gln Arg Gln Lys Lys Val Thr Phe Asp Arg Leu Gln Val Leu Asp Ser
 50                  55                  60 cat tac cag gac gta ctc aag gag gtt aaa gca gcg gcg tca aaa gtg      240
His Tyr Gln Asp Val Leu Lys Glu Val Lys Ala Ala Ala Ser Lys Val
 65                  70                  75                  80 aag gct aac ttg cta tcc gta gag gaa gct tgc agc ctg acg ccc cca      288
Lys Ala Asn Leu Leu Ser Val Glu Glu Ala Cys Ser Leu Thr Pro Pro
                 85                  90                  95 cac tca gcc aaa tcc aag ttt ggt tat ggg gca aaa gac gtc cgt tgc      336
His Ser Ala Lys Ser Lys Phe Gly Tyr Gly Ala Lys Asp Val Arg Cys
                100                 105                 110 cat gcc aga aag gcc gta acc cac atc aac tcc gtg tgg aaa gac ctt      384
His Ala Arg Lys Ala Val Thr His Ile Asn Ser Val Trp Lys Asp Leu
            115                 120                 125 ctg gaa gac aat gta aca cca ata gac act acc atc atg gct aag aac      432
Leu Glu Asp Asn Val Thr Pro Ile Asp Thr Thr Ile Met Ala Lys Asn
130                 135                 140 gag gtt ttc tgc gtt cag cct gag aag ggg ggt cgt aag cca gct cgt      480
Glu Val Phe Cys Val Gln Pro Glu Lys Gly Gly Arg Lys Pro Ala Arg
145                 150                 155                 160 ctc atc gtg ttc ccc gat ctg ggc gtg cgc gtg tgc gaa aag atg gct      528
Leu Ile Val Phe Pro Asp Leu Gly Val Arg Val Cys Glu Lys Met Ala
                165                 170                 175 ttg tac gac gtg gtt acc aag ctc ccc ttg gcc gtg atg gga agc tcc      576
Leu Tyr Asp Val Val Thr Lys Leu Pro Leu Ala Val Met Gly Ser Ser
                180                 185                 190 tac gga ttc caa tac tca cca gga cag cgg gtt gaa ttc ctc gtg caa      624
Tyr Gly Phe Gln Tyr Ser Pro Gly Gln Arg Val Glu Phe Leu Val Gln
            195                 200                 205 gcg tgg aag tcc aag aaa acc cca atg ggg ttc tcg tat gat acc cgc      672
Ala Trp Lys Ser Lys Lys Thr Pro Met Gly Phe Ser Tyr Asp Thr Arg
210                 215                 220 tgc ttt gac tcc aca gtc act gag agc gac atc cgt acg gag gag gca      720
Cys Phe Asp Ser Thr Val Thr Glu Ser Asp Ile Arg Thr Glu Glu Ala
225                 230                 235                 240 atc tac caa tgt tgt gac ctc gac ccc caa gcc cgc gtg gcc atc aag      768
Ile Tyr Gln Cys Cys Asp Leu Asp Pro Gln Ala Arg Val Ala Ile Lys
                245                 250                 255 tcc ctc acc gag agg ctt tat gtt ggg ggc cct ctt acc aat tca agg      816
Ser Leu Thr Glu Arg Leu Tyr Val Gly Gly Pro Leu Thr Asn Ser Arg
                260                 265                 270 ggg gag aac tgc ggc tat cgc agg tgc cgc gcg agc ggc gta ctg aca      864
Gly Glu Asn Cys Gly Tyr Arg Arg Cys Arg Ala Ser Gly Val Leu Thr
            275                 280                 285 act agc tgc ggt aac acc ctc act tgc tac atc aag gcc cgg gca gcc      912
Thr Ser Cys Gly Asn Thr Leu Thr Cys Tyr Ile Lys Ala Arg Ala Ala
290                 295                 300 tgt cga gcc gca ggg ctc cag gac tgc acc atg ctc gtg tgt ggc gac      960
Cys Arg Ala Ala Gly Leu Gln Asp Cys Thr Met Leu Val Cys Gly Asp
305                 310                 315                 320 gac tta gtc gtt atc tgt gaa agc gcg ggg gtc cag gag gac gcg gcg     1008
Asp Leu Val Val Ile Cys Glu Ser Ala Gly Val Gln Glu Asp Ala Ala
                325                 330                 335 agc ctg aga gcc ttc acg gag gct atg acc agg tac tcc gcc ccc ccc     1056
Ser Leu Arg Ala Phe Thr Glu Ala Met Thr Arg Tyr Ser Ala Pro Pro
            340                 345                 350
```

```
ggg gac ccc cca caa cca gaa tac gac ttg gag ctc ata aca tca tgc    1104
Gly Asp Pro Pro Gln Pro Glu Tyr Asp Leu Glu Leu Ile Thr Ser Cys
            355                 360                 365 tcc tcc aac gtg tca gtc gcc cac gac ggc gct gga aag agg gtc tac    1152
Ser Ser Asn Val Ser Val Ala His Asp Gly Ala Gly Lys Arg Val Tyr
        370                 375                 380 tac ctc acc cgt gac cct aca acc ccc ctc gcg aga gct gcg tgg gag    1200
Tyr Leu Thr Arg Asp Pro Thr Thr Pro Leu Ala Arg Ala Ala Trp Glu
385                 390                 395                 400 aca gca aga cac act cca gtc aat tcc tgg cta ggc aac ata atc atg    1248
Thr Ala Arg His Thr Pro Val Asn Ser Trp Leu Gly Asn Ile Ile Met
            405                 410                 415 ttt gcc ccc aca ctg tgg gcg agg atg ata ctg atg acc cat ttc ttt    1296
Phe Ala Pro Thr Leu Trp Ala Arg Met Ile Leu Met Thr His Phe Phe
        420                 425                 430 agc gtc ctt ata gcc agg gac cag ctt gaa cag gcc ctc gat tgc gag    1344
Ser Val Leu Ile Ala Arg Asp Gln Leu Glu Gln Ala Leu Asp Cys Glu
            435                 440                 445 atc tac ggg gcc tgc tac tcc ata gaa cca ctt gat cta cct cca atc    1392
Ile Tyr Gly Ala Cys Tyr Ser Ile Glu Pro Leu Asp Leu Pro Pro Ile
450                 455                 460 att caa aga ctc cat ggc ctc agc gca ttt tca ctc cac agt tac tct    1440
Ile Gln Arg Leu His Gly Leu Ser Ala Phe Ser Leu His Ser Tyr Ser
465                 470                 475                 480 cca ggt gaa att aat agg gtg gcc gca tgc ctc aga aaa ctt ggg gta    1488
Pro Gly Glu Ile Asn Arg Val Ala Ala Cys Leu Arg Lys Leu Gly Val
            485                 490                 495 ccg ccc ttg cga gct tgg aga cac cgg gcc cgg agc gtc cgc gct agg    1536
Pro Pro Leu Arg Ala Trp Arg His Arg Ala Arg Ser Val Arg Ala Arg
        500                 505                 510 ctt ctg gcc aga gga ggc agg gct gcc ata tgt ggc aag tac ctc ttc    1584
Leu Leu Ala Arg Gly Gly Arg Ala Ala Ile Cys Gly Lys Tyr Leu Phe
            515                 520                 525 aac tgg gca gta aga aca aag ctc aaa ctc act cca ata gcg gcc gct    1632
Asn Trp Ala Val Arg Thr Lys Leu Lys Leu Thr Pro Ile Ala Ala Ala
530                 535                 540 ggc cag ctg gac ttg tcc ggc tgg ttc acg gct ggc tac agc ggg gga    1680
Gly Gln Leu Asp Leu Ser Gly Trp Phe Thr Ala Gly Tyr Ser Gly Gly
545                 550                 555                 560 gac att tat cac agc gtg tct cat gcc cgg ccc cgc tgg atc tgg ttt    1728
Asp Ile Tyr His Ser Val Ser His Ala Arg Pro Arg Trp Ile Trp Phe
            565                 570                 575 tgc cta ctc ctg ctt gct gca ggg gta ggc atc tac ctc ctc ccc aac    1776
Cys Leu Leu Leu Leu Ala Ala Gly Val Gly Ile Tyr Leu Leu Pro Asn
        580                 585                 590 cga tga ggatcc                                                     1788
Arg

<210> SEQ ID NO 2
<211> LENGTH: 593
<212> TYPE: PRT
<213> ORGANISM: Hepatitis C virus

<400> SEQUENCE: 2

Met Ala Ser Met Ser Tyr Ser Trp Thr Gly Ala Leu Val Thr Pro Cys
1               5                   10                  15

Ala Ala Glu Glu Gln Lys Leu Pro Ile Asn Ala Leu Ser Asn Ser Leu
            20                  25                  30

Leu Arg His His Asn Leu Val Tyr Ser Thr Thr Ser Arg Ser Ala Cys
        35                  40                  45
```

```
Gln Arg Gln Lys Lys Val Thr Phe Asp Arg Leu Gln Val Leu Asp Ser
         50                  55                  60

His Tyr Gln Asp Val Leu Lys Glu Val Lys Ala Ala Ser Lys Val
 65                  70                  75                  80

Lys Ala Asn Leu Leu Ser Val Glu Glu Ala Cys Ser Leu Thr Pro Pro
                     85                  90                  95

His Ser Ala Lys Ser Lys Phe Gly Tyr Gly Ala Lys Asp Val Arg Cys
                    100                 105                 110

His Ala Arg Lys Ala Val Thr His Ile Asn Ser Val Trp Lys Asp Leu
            115                 120                 125

Leu Glu Asp Asn Val Thr Pro Ile Asp Thr Thr Ile Met Ala Lys Asn
    130                 135                 140

Glu Val Phe Cys Val Gln Pro Glu Lys Gly Gly Arg Lys Pro Ala Arg
145                 150                 155                 160

Leu Ile Val Phe Pro Asp Leu Gly Val Arg Val Cys Glu Lys Met Ala
                165                 170                 175

Leu Tyr Asp Val Val Thr Lys Leu Pro Leu Ala Val Met Gly Ser Ser
                180                 185                 190

Tyr Gly Phe Gln Tyr Ser Pro Gly Gln Arg Val Glu Phe Leu Val Gln
            195                 200                 205

Ala Trp Lys Ser Lys Lys Thr Pro Met Gly Phe Ser Tyr Asp Thr Arg
    210                 215                 220

Cys Phe Asp Ser Thr Val Thr Glu Ser Asp Ile Arg Thr Glu Glu Ala
225                 230                 235                 240

Ile Tyr Gln Cys Cys Asp Leu Asp Pro Gln Ala Arg Val Ala Ile Lys
                245                 250                 255

Ser Leu Thr Glu Arg Leu Tyr Val Gly Gly Pro Leu Thr Asn Ser Arg
            260                 265                 270

Gly Glu Asn Cys Gly Tyr Arg Arg Cys Arg Ala Ser Gly Val Leu Thr
        275                 280                 285

Thr Ser Cys Gly Asn Thr Leu Thr Cys Tyr Ile Lys Ala Arg Ala Ala
    290                 295                 300

Cys Arg Ala Ala Gly Leu Gln Asp Cys Thr Met Leu Val Cys Gly Asp
305                 310                 315                 320

Asp Leu Val Val Ile Cys Glu Ser Ala Gly Val Gln Glu Asp Ala Ala
                325                 330                 335

Ser Leu Arg Ala Phe Thr Glu Ala Met Thr Arg Tyr Ser Ala Pro Pro
            340                 345                 350

Gly Asp Pro Pro Gln Pro Glu Tyr Asp Leu Glu Leu Ile Thr Ser Cys
        355                 360                 365

Ser Ser Asn Val Ser Val Ala His Asp Gly Ala Gly Lys Arg Val Tyr
    370                 375                 380

Tyr Leu Thr Arg Asp Pro Thr Thr Pro Leu Ala Arg Ala Ala Trp Glu
385                 390                 395                 400

Thr Ala Arg His Thr Pro Val Asn Ser Trp Leu Gly Asn Ile Ile Met
                405                 410                 415

Phe Ala Pro Thr Leu Trp Ala Arg Met Ile Leu Met Thr His Phe Phe
                420                 425                 430

Ser Val Leu Ile Ala Arg Asp Gln Leu Glu Gln Ala Leu Asp Cys Glu
        435                 440                 445

Ile Tyr Gly Ala Cys Tyr Ser Ile Glu Pro Leu Asp Leu Pro Pro Ile
    450                 455                 460
```

```
Ile Gln Arg Leu His Gly Leu Ser Ala Phe Ser Leu His Ser Tyr Ser
465                 470                 475                 480

Pro Gly Glu Ile Asn Arg Val Ala Ala Cys Leu Arg Lys Leu Gly Val
                485                 490                 495

Pro Pro Leu Arg Ala Trp Arg His Arg Ala Arg Ser Val Arg Ala Arg
            500                 505                 510

Leu Leu Ala Arg Gly Gly Arg Ala Ala Ile Cys Gly Lys Tyr Leu Phe
        515                 520                 525

Asn Trp Ala Val Arg Thr Lys Leu Lys Leu Thr Pro Ile Ala Ala Ala
    530                 535                 540

Gly Gln Leu Asp Leu Ser Gly Trp Phe Thr Ala Gly Tyr Ser Gly Gly
545                 550                 555                 560

Asp Ile Tyr His Ser Val Ser His Ala Arg Pro Arg Trp Ile Trp Phe
                565                 570                 575

Cys Leu Leu Leu Leu Ala Ala Gly Val Gly Ile Tyr Leu Leu Pro Asn
            580                 585                 590

Arg

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 3
atagctagca tgtcttactc ttggacagg                                    29

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4
ataggatcct catcggttgg ggaggagg                                     28

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Modified
      N-terminus of Hepatitis NS5B region.

<400> SEQUENCE: 5

Ala Ser Met Ser Tyr
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Modified
      N-terminal sequence of HCV NS5B.

<400> SEQUENCE: 6

Met Ala Ser Met Ser Tyr
 1               5
```

```
<210> SEQ ID NO 7
<211> LENGTH: 4
<212> TYPE: PRT
<213> ORGANISM: Hepatitis C virus

<400> SEQUENCE: 7

Ser Met Ser Tyr
  1

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Modified
      N-terminus sequence of HCV NS5B.

<400> SEQUENCE: 8

Ala Ser Met Ser Tyr Ser Trp Thr
  1               5

<210> SEQ ID NO 9
<211> LENGTH: 105
<212> TYPE: DNA
<213> ORGANISM: Artificial Sequence
<220> FEATURE:
<223> OTHER INFORMATION: Description of Artificial Sequence: Cloning
      site in pET-11A where the 5'end of the PCR amplified
      NS5B gene was inserted.

<400> SEQUENCE: 9
gggagaccac aacggtttcc ctctagaaat aattttgttt aactttaaga aggagatata      60
catatggcta gcatgactgg tggacagcaa atgggtcgcg gatcc                     105

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Amino acid
      sequence of the cloning site in pET-11A where the
      5' end of the PCR amplified NS5B gene was
      inserted.

<400> SEQUENCE: 10

Met Ala Ser Met Thr Gly Gly Gln Gln Met Gly Arg Gly Ser
  1               5                  10

<210> SEQ ID NO 11
<211> LENGTH: 1782
<212> TYPE: DNA
<213> ORGANISM: Hepatitis C virus
<220> FEATURE:
<221> NAME/KEY: CDS
<222> LOCATION: (1)..(1779)

<400> SEQUENCE: 11 atg gct agc atg tcc tac aca tgg aca ggc gcc ttg atc acg cca tgc        48
Met Ala Ser Met Ser Tyr Thr Trp Thr Gly Ala Leu Ile Thr Pro Cys
  1               5                  10                  15 gcc gcg gag gaa caa aag ctg ccc atc aat gcg ttg agc aac tcc ttg        96
Ala Ala Glu Glu Gln Lys Leu Pro Ile Asn Ala Leu Ser Asn Ser Leu
             20                  25                  30 ctg cgc cac cat aac atg gtc tat gcc aca aca tcc cgc agc gca agc       144
Leu Arg His His Asn Met Val Tyr Ala Thr Thr Ser Arg Ser Ala Ser
         35                  40                  45
```

-continued

| | |
|---|---|
| caa cgg cag aag aag gtc acc ttt gac aga ctg caa gtc ctg gac gat<br>Gln Arg Gln Lys Lys Val Thr Phe Asp Arg Leu Gln Val Leu Asp Asp<br>50              55                  60 | 192 |
| cac tac cag gac gtg ctc aag gag atg aag gcg aag gcg tcc aca gtt<br>His Tyr Gln Asp Val Leu Lys Glu Met Lys Ala Lys Ala Ser Thr Val<br>65                  70                  75                  80 | 240 |
| aag gct aaa ctt cta tcc gta gaa gaa gcc tgt aag ctg acg ccc cca<br>Lys Ala Lys Leu Leu Ser Val Glu Glu Ala Cys Lys Leu Thr Pro Pro<br>                    85                  90                  95 | 288 |
| cat tcg gcc aga tcc aaa ttt ggc tat ggg gca aag gac gtc cgg aac<br>His Ser Ala Arg Ser Lys Phe Gly Tyr Gly Ala Lys Asp Val Arg Asn<br>        100                 105                 110 | 336 |
| cta tcc agc agg gcc gtt aac cac atc cgc tcc gtg tgg aag gac ctg<br>Leu Ser Ser Arg Ala Val Asn His Ile Arg Ser Val Trp Lys Asp Leu<br>    115                 120                 125 | 384 |
| ctg gaa gac act gca aca cca att gac acc acc atc atg gca aaa aat<br>Leu Glu Asp Thr Ala Thr Pro Ile Asp Thr Thr Ile Met Ala Lys Asn<br>130                 135                 140 | 432 |
| gag gtt ttc tgc gtc caa cca gag aaa gga ggc cgc aag cca gct cgc<br>Glu Val Phe Cys Val Gln Pro Glu Lys Gly Gly Arg Lys Pro Ala Arg<br>145                 150                 155                 160 | 480 |
| ctt atc gtg ttc cca gat ttg gga gtt cgt gtg tgc gag aag atg gcc<br>Leu Ile Val Phe Pro Asp Leu Gly Val Arg Val Cys Glu Lys Met Ala<br>            165                 170                 175 | 528 |
| ctt tac gac gtg gtc tcc acc ctt cct cag gcc gtg atg ggc tcc tca<br>Leu Tyr Asp Val Val Ser Thr Leu Pro Gln Ala Val Met Gly Ser Ser<br>        180                 185                 190 | 576 |
| tac gga ttc cag tac tct cct gga cag cgg gtt gag ttc ctg gtg aat<br>Tyr Gly Phe Gln Tyr Ser Pro Gly Gln Arg Val Glu Phe Leu Val Asn<br>    195                 200                 205 | 624 |
| gcc tgg aag tca aag aaa tgc cct atg ggc ttt gca tat gac acc cgc<br>Ala Trp Lys Ser Lys Lys Cys Pro Met Gly Phe Ala Tyr Asp Thr Arg<br>210                 215                 220 | 672 |
| tgt ttc gac tca aca gtc aca gag agt gac atc cgt gtt gag gag tca<br>Cys Phe Asp Ser Thr Val Thr Glu Ser Asp Ile Arg Val Glu Glu Ser<br>225                 230                 235                 240 | 720 |
| atc tac caa tgt tgt gac ttg gcc ccc gaa gcc aga cag gcc ata agg<br>Ile Tyr Gln Cys Cys Asp Leu Ala Pro Glu Ala Arg Gln Ala Ile Arg<br>            245                 250                 255 | 768 |
| tcg ctc aca gag cgg ctt tac atc ggg ggc ccc ctg act aac tca aaa<br>Ser Leu Thr Glu Arg Leu Tyr Ile Gly Gly Pro Leu Thr Asn Ser Lys<br>        260                 265                 270 | 816 |
| ggg cag aac tgc ggt tat cgc cgg tgc cgc gcg agc ggt gtg ctg acg<br>Gly Gln Asn Cys Gly Tyr Arg Arg Cys Arg Ala Ser Gly Val Leu Thr<br>    275                 280                 285 | 864 |
| act agc tgc ggt aat acc ctc aca tgt tac ttg aag gcc act gcg gcc<br>Thr Ser Cys Gly Asn Thr Leu Thr Cys Tyr Leu Lys Ala Thr Ala Ala<br>290                 295                 300 | 912 |
| tgt cga gct gcc aag ctc cag gac tgc aca atg ctc gtg tgc gga gac<br>Cys Arg Ala Ala Lys Leu Gln Asp Cys Thr Met Leu Val Cys Gly Asp<br>305                 310                 315                 320 | 960 |
| gac ctt gtc gtt atc tgt gaa agc gcg gga acc cag gag gac gcg gca<br>Asp Leu Val Val Ile Cys Glu Ser Ala Gly Thr Gln Glu Asp Ala Ala<br>            325                 330                 335 | 1008 |
| agc cta cga gtc ttc acg gag gct atg act agg tac tct gcc ccc ccc<br>Ser Leu Arg Val Phe Thr Glu Ala Met Thr Arg Tyr Ser Ala Pro Pro<br>        340                 345                 350 | 1056 |
| ggg gac ccg cct caa cca gaa tac gac ttg gag ttg ata aca tca tgc<br>Gly Asp Pro Pro Gln Pro Glu Tyr Asp Leu Glu Leu Ile Thr Ser Cys<br>    355                 360                 365 | 1104 |

-continued

```
tcc tcc aat gtg tcg gtc gcg cac gac gca tct ggc aaa agg gta tac      1152
Ser Ser Asn Val Ser Val Ala His Asp Ala Ser Gly Lys Arg Val Tyr
    370                 375                 380 tac ctc acc cgt gac ccc acc acc ccc ctt gcg agg gct gcg tgg gag      1200
Tyr Leu Thr Arg Asp Pro Thr Thr Pro Leu Ala Arg Ala Ala Trp Glu
385                 390                 395                 400 aca gct aga cac act cca gtc aac tcc tgg cta ggc aac atc atc atg      1248
Thr Ala Arg His Thr Pro Val Asn Ser Trp Leu Gly Asn Ile Ile Met
            405                 410                 415 tat gcg cct acc tta tgg gca agg atg att ctg atg act cac ttc ttc      1296
Tyr Ala Pro Thr Leu Trp Ala Arg Met Ile Leu Met Thr His Phe Phe
                420                 425                 430 tcc atc ctt cta gcc cag gag caa ctt gaa aag gcc cta gac tgt cag      1344
Ser Ile Leu Leu Ala Gln Glu Gln Leu Glu Lys Ala Leu Asp Cys Gln
            435                 440                 445 atc tac ggg gcc tgc tac tcc att gag cca ctt gac cta cct cag atc      1392
Ile Tyr Gly Ala Cys Tyr Ser Ile Glu Pro Leu Asp Leu Pro Gln Ile
        450                 455                 460 att caa cga ctc cat ggt ctt agc gca ttc tca ctc cac agt tac tct      1440
Ile Gln Arg Leu His Gly Leu Ser Ala Phe Ser Leu His Ser Tyr Ser
465                 470                 475                 480 cca ggt gaa atc aat agg gtg gct tca tgc ctc agg aaa ctt ggg gta      1488
Pro Gly Glu Ile Asn Arg Val Ala Ser Cys Leu Arg Lys Leu Gly Val
                485                 490                 495 ccg ccc ttg cga gtc tgg aga cat cgg gcc aga agt gtc cgc gct aag      1536
Pro Pro Leu Arg Val Trp Arg His Arg Ala Arg Ser Val Arg Ala Lys
            500                 505                 510 cta ctg tcc cag ggg ggg agg gcc gcc act tgt ggc aaa tac ctc ttc      1584
Leu Leu Ser Gln Gly Gly Arg Ala Ala Thr Cys Gly Lys Tyr Leu Phe
        515                 520                 525 aac tgg gca gta aaa acc aag ctc aaa ctc act cca atc ccg gct gcg      1632
Asn Trp Ala Val Lys Thr Lys Leu Lys Leu Thr Pro Ile Pro Ala Ala
530                 535                 540 tcc cag ttg gat tta tcc gga tgg gtt aca gct ggt tac agc ggg gga      1680
Ser Gln Leu Asp Leu Ser Gly Trp Val Thr Ala Gly Tyr Ser Gly Gly
545                 550                 555                 560 gac ata tat cac agc ctg tct cgt gcc cga ccc cgc tgg ttc atg tgg      1728
Asp Ile Tyr His Ser Leu Ser Arg Ala Arg Pro Arg Trp Phe Met Trp
                565                 570                 575 tgc cta ctc cta ctt tct gta ggg gta ggc atc tac ctg ctc ccc aac      1776
Cys Leu Leu Leu Leu Ser Val Gly Val Gly Ile Tyr Leu Leu Pro Asn
            580                 585                 590 cgg tga                                                               1782
Arg
```

<210> SEQ ID NO 12
<211> LENGTH: 593
<212> TYPE: PRT
<213> ORGANISM: Hepatitis C virus

<400> SEQUENCE: 12

```
Met Ala Ser Met Ser Tyr Thr Trp Thr Gly Ala Leu Ile Thr Pro Cys
1               5                   10                  15

Ala Ala Glu Glu Gln Lys Leu Pro Ile Asn Ala Leu Ser Asn Ser Leu
            20                  25                  30

Leu Arg His His Asn Met Val Tyr Ala Thr Thr Ser Arg Ser Ala Ser
        35                  40                  45

Gln Arg Gln Lys Lys Val Thr Phe Asp Arg Leu Gln Val Leu Asp Asp
    50                  55                  60
```

```
His Tyr Gln Asp Val Leu Lys Glu Met Lys Ala Lys Ala Ser Thr Val
 65                  70                  75                  80

Lys Ala Lys Leu Leu Ser Val Glu Glu Ala Cys Lys Leu Thr Pro Pro
                 85                  90                  95

His Ser Ala Arg Ser Lys Phe Gly Tyr Gly Ala Lys Asp Val Arg Asn
            100                 105                 110

Leu Ser Ser Arg Ala Val Asn His Ile Arg Ser Val Trp Lys Asp Leu
        115                 120                 125

Leu Glu Asp Thr Ala Thr Pro Ile Asp Thr Thr Ile Met Ala Lys Asn
    130                 135                 140

Glu Val Phe Cys Val Gln Pro Glu Lys Gly Gly Arg Lys Pro Ala Arg
145                 150                 155                 160

Leu Ile Val Phe Pro Asp Leu Gly Val Arg Val Cys Glu Lys Met Ala
                165                 170                 175

Leu Tyr Asp Val Val Ser Thr Leu Pro Gln Ala Val Met Gly Ser Ser
            180                 185                 190

Tyr Gly Phe Gln Tyr Ser Pro Gly Gln Arg Val Glu Phe Leu Val Asn
        195                 200                 205

Ala Trp Lys Ser Lys Lys Cys Pro Met Gly Phe Ala Tyr Asp Thr Arg
    210                 215                 220

Cys Phe Asp Ser Thr Val Thr Glu Ser Asp Ile Arg Val Glu Glu Ser
225                 230                 235                 240

Ile Tyr Gln Cys Cys Asp Leu Ala Pro Glu Ala Arg Gln Ala Ile Arg
                245                 250                 255

Ser Leu Thr Glu Arg Leu Tyr Ile Gly Gly Pro Leu Thr Asn Ser Lys
            260                 265                 270

Gly Gln Asn Cys Gly Tyr Arg Arg Cys Arg Ala Ser Gly Val Leu Thr
        275                 280                 285

Thr Ser Cys Gly Asn Thr Leu Thr Cys Tyr Leu Lys Ala Thr Ala Ala
    290                 295                 300

Cys Arg Ala Ala Lys Leu Gln Asp Cys Thr Met Leu Val Cys Gly Asp
305                 310                 315                 320

Asp Leu Val Val Ile Cys Glu Ser Ala Gly Thr Gln Glu Asp Ala Ala
                325                 330                 335

Ser Leu Arg Val Phe Thr Glu Ala Met Thr Arg Tyr Ser Ala Pro Pro
            340                 345                 350

Gly Asp Pro Pro Gln Pro Glu Tyr Asp Leu Glu Leu Ile Thr Ser Cys
        355                 360                 365

Ser Ser Asn Val Ser Val Ala His Asp Ala Ser Gly Lys Arg Val Tyr
    370                 375                 380

Tyr Leu Thr Arg Asp Pro Thr Thr Pro Leu Ala Arg Ala Ala Trp Glu
385                 390                 395                 400

Thr Ala Arg His Thr Pro Val Asn Ser Trp Leu Gly Asn Ile Ile Met
                405                 410                 415

Tyr Ala Pro Thr Leu Trp Ala Arg Met Ile Leu Met Thr His Phe Phe
            420                 425                 430

Ser Ile Leu Leu Ala Gln Glu Gln Leu Glu Lys Ala Leu Asp Cys Gln
        435                 440                 445

Ile Tyr Gly Ala Cys Tyr Ser Ile Glu Pro Leu Asp Leu Pro Gln Ile
    450                 455                 460

Ile Gln Arg Leu His Gly Leu Ser Ala Phe Ser Leu His Ser Tyr Ser
465                 470                 475                 480
```

```
Pro Gly Glu Ile Asn Arg Val Ala Ser Cys Leu Arg Lys Leu Gly Val
            485                 490                 495

Pro Pro Leu Arg Val Trp Arg His Arg Ala Arg Ser Val Arg Ala Lys
        500                 505                 510

Leu Leu Ser Gln Gly Gly Arg Ala Ala Thr Cys Gly Lys Tyr Leu Phe
        515                 520                 525

Asn Trp Ala Val Lys Thr Lys Leu Lys Leu Thr Pro Ile Pro Ala Ala
        530                 535                 540

Ser Gln Leu Asp Leu Ser Gly Trp Val Thr Ala Gly Tyr Ser Gly Gly
545                 550                 555                 560

Asp Ile Tyr His Ser Leu Ser Arg Ala Arg Pro Arg Trp Phe Met Trp
                565                 570                 575

Cys Leu Leu Leu Leu Ser Val Gly Val Gly Ile Tyr Leu Leu Pro Asn
            580                 585                 590

Arg

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 13
ctggacgatc actacaggga cgtgctcaag gag                          33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 14
ctccttgagc acgtccctgt agtgatcgtc cag                          33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 15
ctgctggaag acactgaaac accaattgac acc                          33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 16
ggtgtcaatt ggtgtttcag tgtcttccag cag                          33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 17
cggaacctat ccagcaaggc cgttaaccac atc                                    33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 18
gatgtggtta acggccttgc tggataggtt ccg                                    33

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 19
gaaatgccct atgggctttt catatgacac ccgctgtttc g                           41

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 20
cgaaacagcg ggtgtcatat gaaaagccca tagggcattt c                           41

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 21
ctcaacagtc acagagaatg acatccgtgt tgagg                                  35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 22
cctcaacagg gatgtcattc tctgtgactg ttgag                                  35

<210> SEQ ID NO 23
<211> LENGTH: 593
<212> TYPE: PRT
<213> ORGANISM: Hepatitis C virus

<400> SEQUENCE: 23

Met Ala Ser Met Ser Tyr Thr Trp Thr Gly Ala Leu Ile Thr Pro Cys
 1               5                  10                  15

Ala Ala Glu Glu Gln Lys Leu Pro Ile Asn Ala Leu Ser Asn Ser Leu
             20                  25                  30

Leu Arg His His Asn Met Val Tyr Ala Thr Thr Ser Arg Ser Ala Ser
```

-continued

```
                35                  40                  45
Leu Arg Gln Lys Lys Val Thr Phe Asp Arg Leu Gln Val Leu Asp Asp
 50                  55                  60
His Tyr Gln Asp Val Leu Lys Glu Met Lys Ala Lys Ala Ser Thr Val
 65                  70                  75                  80
Lys Ala Lys Leu Leu Ser Val Glu Glu Ala Cys Lys Leu Thr Pro Pro
                 85                  90                  95
His Ser Ala Lys Ser Lys Phe Gly Tyr Gly Ala Lys Asp Val Arg Asn
                100                 105                 110
Leu Ser Ser Arg Ala Val Asn His Ile His Ser Val Trp Lys Asp Leu
                115                 120                 125
Leu Glu Asp Thr Glu Thr Pro Ile Asp Thr Thr Ile Met Ala Lys Asn
130                 135                 140
Glu Val Phe Cys Val Gln Pro Glu Lys Gly Gly Arg Lys Pro Ala Arg
145                 150                 155                 160
Leu Ile Val Phe Pro Asp Leu Gly Val Arg Val Cys Glu Lys Met Ala
                165                 170                 175
Leu Tyr Asp Val Val Ser Thr Leu Pro Gln Val Val Met Gly Ser Ser
                180                 185                 190
Tyr Gly Phe Gln Tyr Ser Pro Gly Gln Arg Val Glu Phe Leu Val Asn
                195                 200                 205
Thr Trp Lys Ser Lys Lys Cys Pro Met Gly Phe Ser Tyr Asp Thr Arg
210                 215                 220
Cys Phe Asp Ser Thr Val Thr Glu Asn Asp Ile Arg Val Glu Glu Ser
225                 230                 235                 240
Ile Tyr Gln Cys Cys Asp Leu Ala Pro Glu Ala Arg Gln Ala Ile Lys
                245                 250                 255
Ser Leu Thr Glu Arg Leu Tyr Ile Gly Gly Pro Leu Thr Asn Ser Lys
                260                 265                 270
Gly Gln Asn Cys Gly Tyr Arg Arg Cys Arg Ala Ser Gly Val Leu Thr
                275                 280                 285
Thr Ser Cys Gly Asn Thr Leu Thr Cys Tyr Leu Lys Ala Ser Ala Ala
290                 295                 300
Cys Arg Ala Ala Lys Leu Gln Asp Cys Thr Met Leu Val Asn Gly Asp
305                 310                 315                 320
Asp Leu Val Val Ile Cys Glu Ser Ala Gly Thr Gln Glu Asp Ala Ala
                325                 330                 335
Ser Leu Arg Val Phe Thr Glu Ala Met Thr Arg Tyr Ser Ala Pro Pro
                340                 345                 350
Gly Asp Pro Pro Gln Pro Glu Tyr Asp Leu Glu Leu Ile Thr Ser Cys
                355                 360                 365
Ser Ser Asn Val Ser Val Ala His Asp Ala Ser Gly Lys Arg Val Tyr
                370                 375                 380
Tyr Leu Thr Arg Asp Pro Thr Thr Pro Leu Ala Arg Ala Ala Trp Glu
385                 390                 395                 400
Thr Ala Arg His Thr Pro Val Asn Ser Trp Leu Gly Asn Ile Ile Met
                405                 410                 415
Tyr Ala Pro Thr Leu Trp Ala Arg Met Ile Leu Met Thr His Phe Phe
                420                 425                 430
Ser Ile Leu Leu Ala Gln Glu Gln Leu Glu Lys Ala Leu Asp Cys Gln
                435                 440                 445
Ile Tyr Gly Ala Cys Tyr Ser Ile Glu Pro Leu Asp Leu Pro Gln Ile
                450                 455                 460
```

-continued

```
Ile Glu Arg Leu His Gly Leu Ser Ala Phe Ser Leu His Ser Tyr Ser
465             470                 475                 480

Pro Gly Glu Ile Asn Arg Val Ala Ser Cys Leu Arg Lys Leu Gly Val
            485                 490                 495

Pro Pro Leu Arg Val Trp Arg His Arg Ala Arg Ser Val Arg Ala Lys
            500             505                 510

Leu Leu Ser Gln Gly Gly Arg Ala Ala Thr Cys Gly Lys Tyr Leu Phe
        515             520                 525

Asn Trp Ala Val Lys Thr Lys Leu Lys Leu Thr Pro Ile Pro Ala Ala
        530             535             540

Ser Gln Leu Asp Leu Ser Gly Trp Val Thr Ala Gly Tyr Ser Gly Gly
545             550             555                 560

Asp Ile Tyr His Ser Leu Ser Arg Ala Arg Pro Arg Trp Phe Met Trp
                565             570                 575

Cys Leu Leu Leu Leu Ser Val Gly Val Gly Ile Tyr Leu Leu Pro Asn
            580             585                 590

Arg
```